(12) United States Patent
Podoleanu

(10) Patent No.: US 8,422,023 B2
(45) Date of Patent: Apr. 16, 2013

(54) COMPACT HIGH RESOLUTION IMAGING APPARATUS

(75) Inventor: Adrian Podoleanu, Canterbury (GB)

(73) Assignee: Optos PLC (GB)

( * ) Notice: Subject to any disclaimer, the term of this patent is extended or adjusted under 35 U.S.C. 154(b) by 741 days.

(21) Appl. No.: 12/307,072

(22) PCT Filed: Jun. 28, 2007

(86) PCT No.: PCT/CA2007/001148
§ 371 (c)(1),
(2), (4) Date: Dec. 3, 2009

(87) PCT Pub. No.: WO2008/000078
PCT Pub. Date: Jan. 3, 2008

(65) Prior Publication Data
US 2010/0067020 A1 Mar. 18, 2010

(30) Foreign Application Priority Data
Jun. 30, 2006 (GB) .................................. 0612974.6

(51) Int. Cl.
*G01B 9/02* (2006.01)
(52) U.S. Cl.
USPC .......................................... 356/479; 356/492

(58) Field of Classification Search .................. 356/479, 356/497, 492; 250/227.19, 227.27
See application file for complete search history.

(56) References Cited

U.S. PATENT DOCUMENTS

| 6,057,920 | A | 5/2000 | Fercher et al. | |
| 6,460,997 | B1 * | 10/2002 | Frey et al. | ..................... 351/211 |
| 7,330,273 | B2 * | 2/2008 | Podoleanu et al. | ........... 356/497 |
| 2002/0163622 | A1 | 11/2002 | Magnin et al. | |
| 2004/0090633 | A1 | 5/2004 | Knüttel | |
| 2005/0231727 | A1 * | 10/2005 | Podoleanu et al. | ........... 356/479 |

FOREIGN PATENT DOCUMENTS

| GB | 2411066 A | 8/2005 |
| WO | 92/19930 A1 | 11/1992 |

* cited by examiner

*Primary Examiner* — Michael A Lyons
(74) *Attorney, Agent, or Firm* — Laubscher & Laubscher, P.C.

(57) ABSTRACT

An optical coherence tomography (OCT) apparatus includes an optical source, an interferometer generating an object beam and a reference beam, a transverse scanner for scanning an object with said object beam, and a processor for generating an OCT image from an OCT signal returned by said interferometer. At least the optical source, the interferometer, and the scanner are mounted on a common translation stage displaceable towards and away from said object. A dynamic focus solution is provided when the scanner and a folded object path are placed on the translation stage.

20 Claims, 13 Drawing Sheets

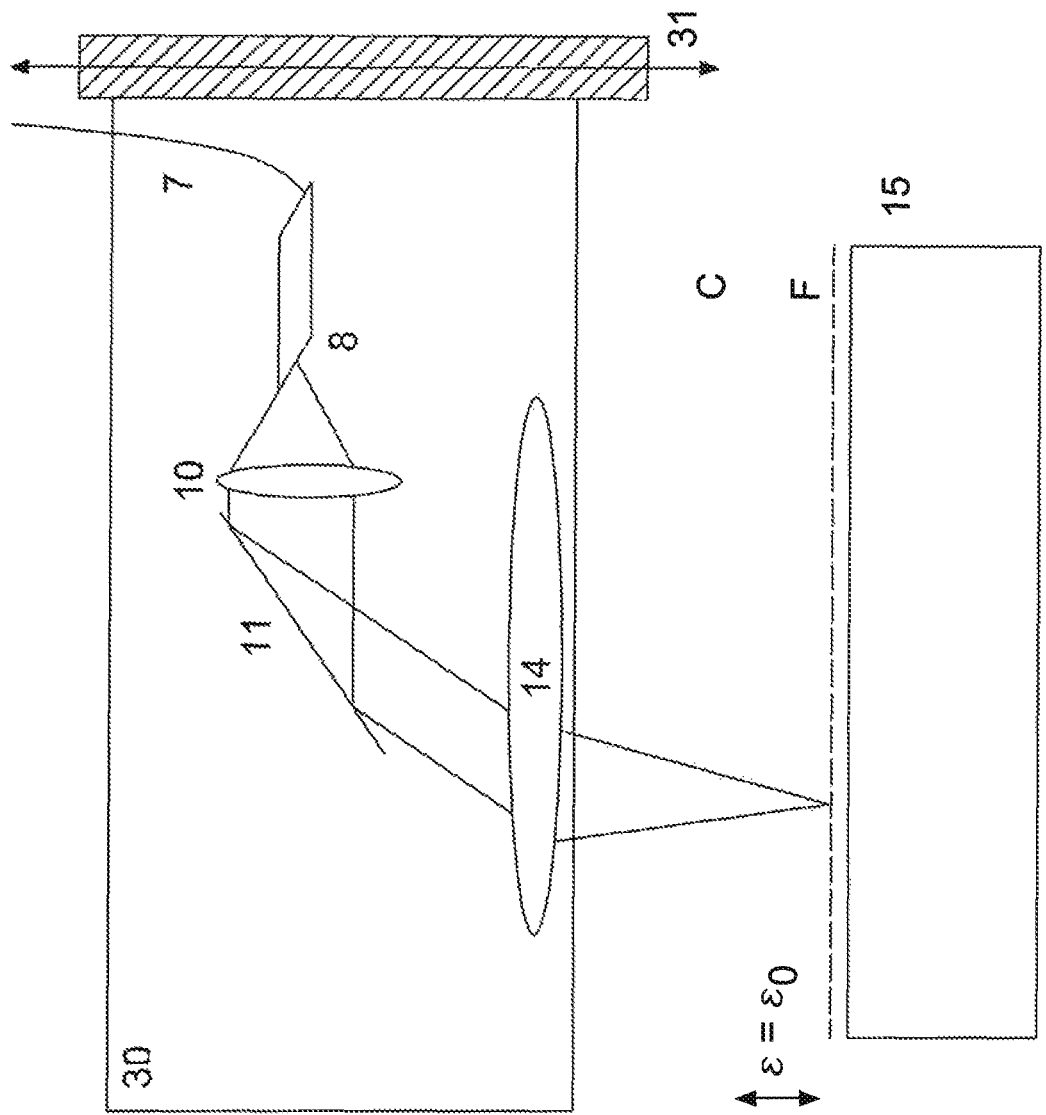

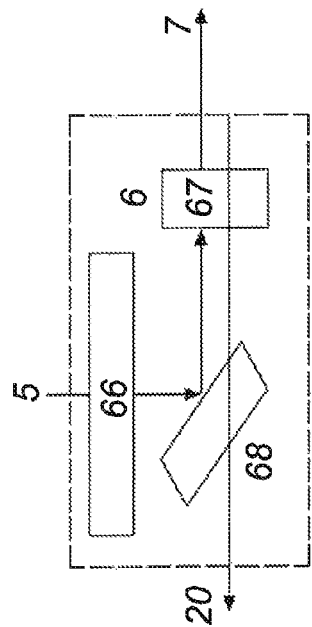
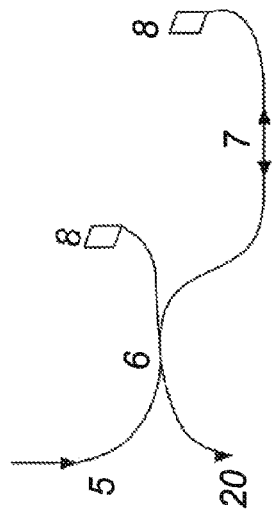
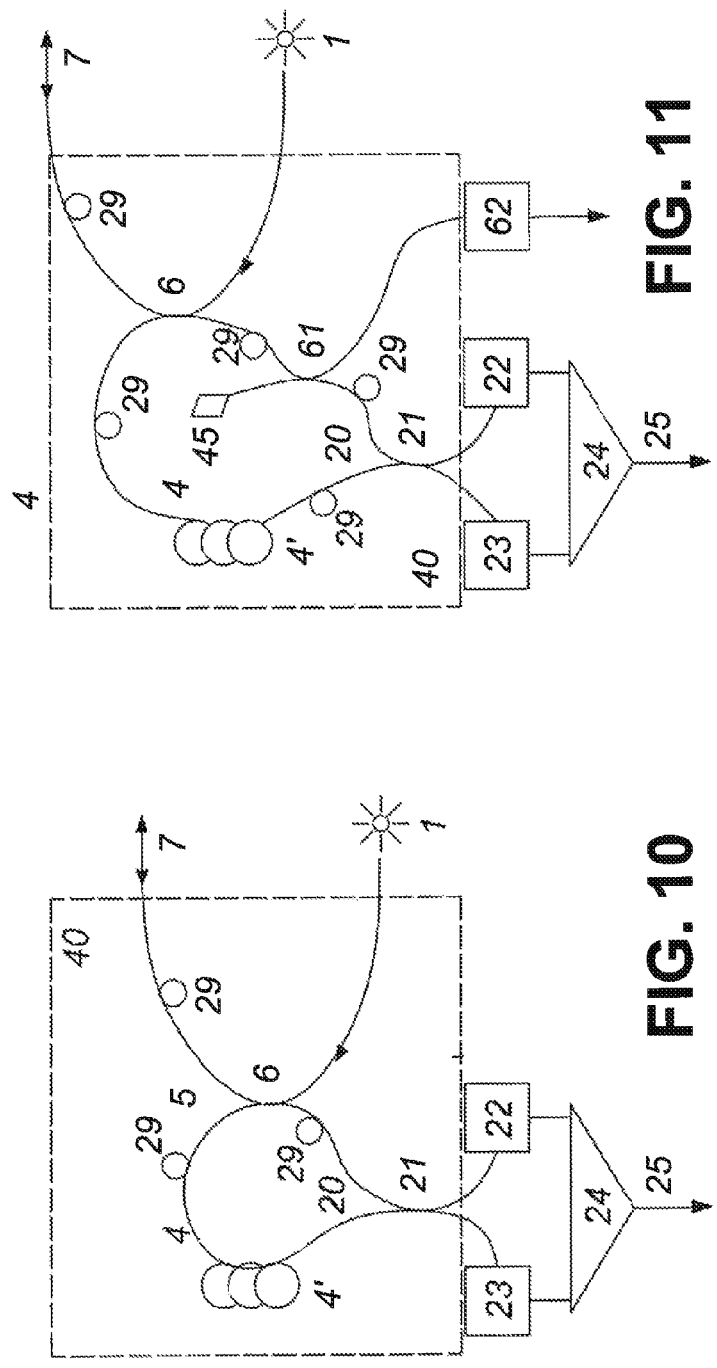
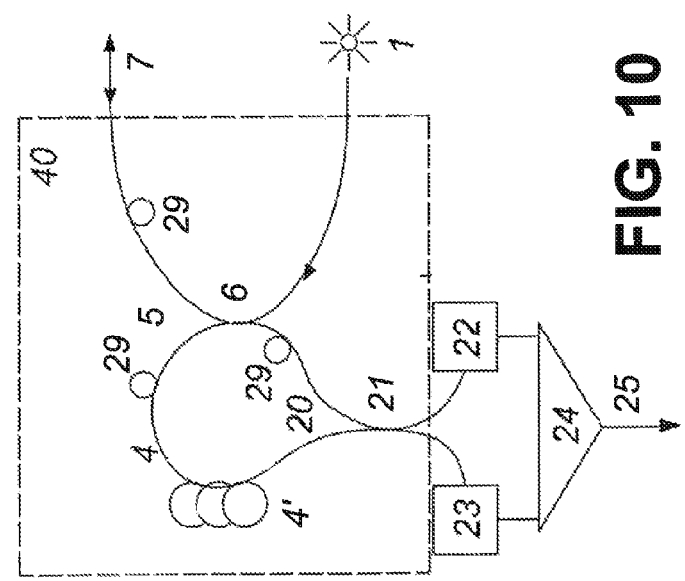

COMPACT HIGH RESOLUTION IMAGING APPARATUS

FIELD OF THE INVENTION

The present invention relates to an optical mapping apparatus, and in particular to an apparatus which can be used to supply images from essentially transparent objects or tissue in general and from the anterior chamber of the eye in special.

BACKGROUND OF THE INVENTION

In the description which follows, reference is made primarily to the eye and the anterior chamber of the eye as the object. This is to be understood as merely exemplary to assist in the description and not as a restriction. Where the term "eye" is used, a more general transparent and scattering object or organ may be sought instead.

Low coherence interferometry is an absolute measurement technique which allows high resolution ranging and characterisation of optoelectronic components as presented in the papers S. A. Al-Chalabi, B. Culshaw and D. E. N. Davies, "Partially coherent sources in interferometric sensors", *First International Conference on Optical Fibre sensors*, 26-28 Apr. 1983, I.E.E. London, pp. 132-135, 1983, R. C. Youngquist, S. Carr, and D. E. N. Davies, "Optical coherence-domain reflectometry: A new optical evaluation technique," *Opt. Lett.* 12(3), pp. 158-160 1987 and H. H. Gilgen, R. P. Novak, R. P. Salathe, W. Hodel, P. Beaud, Submillimeter optical reflectometry", *Lightwave Technol.*, Vol. 7, No. 8, pp. 1225-1233, 1989.

The first application in the biomedical optics field was for the measurement of the eye length as shown in A. F. Fercher, K. Mengedoht and W. Werner, "Eye length measurement by interferometry with partially coherent light", *Opt. Lett.*, Vol. 13, No. 3, (1988), pp. 186-189.

Adding lateral scanning to the scanning in depth, allows acquisition of 3D information from the volume of biologic media. This concept, of adding devices for lateral scanning in an interferometer, has been presented in papers on heterodyne scanning microscopy, such as "Optical heterodyne scanning microscope", published by T. Sawatari in *Applied Optics*, Vol. 12, No. 11, (1973), pp. 2766-2772 and Profilometry with a coherence scanning microscope", by B. S. Lee, T. C. Strand, published in Appl. Opt., 29, 26, 1990, 3784-3788. The later report shows a cross section image from a semiconductor wafer proving the possibility for subsurface imaging.

The potential of the technique for high resolution imaging of the tissue is often referred to as optical coherence tomography (OCT) as presented in D. Huang, E. A. Swanson, C. P. Lin, J. S. Schuman, W. G. Stinson, W. Chang, M. R. Hee, T. Flotte, K. Gregory, C. A. Puliafito and J. G. Fujimoto, 'Optical coherence tomography', *Science* 254, pp. 1178-1181, 1991 and in the paper "Optical coherence tomography" by A. F. Fercher, in *J. Biomed. Opt.*, 1(2), (1996), pp. 157-173. OCT has the potential of achieving high depth resolution, which is determined by the coherence length of the source. For example, optical sources, such as superluminiscent diodes and mode-locked lasers are now available with coherence lengths below 20 μm.

An OCT apparatus is now commercially available (e.g. from Humphrey), which produces longitudinal images only, i.e. images in the planes (x,z) or (y,z), where the z axis is perpendicular to the patient's face and x and y axes are in the plane of the patient's face. Examples of such apparatus for longitudinal imaging are described in U.S. Pat. Nos. 5,493,109, 5,537,162, 5,491,524, 5,469,261, 5,321,501 and 5,459,570 (Swanson).

OCT has also been reported as being capable of providing en-face (or transversal) images, as reported in "Coherence Imaging by Use of a Newton Rings Sampling Function" by A. Gh. Podoleanu, G. M. Dobre, D. J. Webb, D. A. Jackson, published in Opt. Lett., Vol. 21, No. 21, (1996), pp. 1789-1791, "Simultaneous En-face Imaging of Two Layers in Human Retina" Opt. Letters, by A. Gh. Podoleanu, G. M. Dobre, D. J. Webb, D. A. Jackson, published in Opt. Lett., 1997, vol. 22, No. 13, pp. pp. 1039-1041, "En-face Coherence Imaging Using Galvanometer Scanner Modulation" by A. Gh. Podoleanu, G. M. Dobre, D. A. Jackson, Opt. Lett. 23, pp. 147-149, 1998 and in "Transversal and Longitudinal Images from the Retina of the Living Eye Using Low Coherence Reflectometry", by A. Gh. Podoleanu, Mauritius Seeger, George M. Dobre, David J. Webb, David A. Jackson and F. Fitzke, published in the Journal of Biomedical Optics, 3(1), pp. 12-20, 1998 and in the U.S. Pat. No. 5,975,697 (Podoleanu).

As shown in the last paper mentioned above and disclosed in the last patent mentioned above, en-face scanning allows generation of constant depth OCT images as well as cross section OCT images initially reported by using longitudinal OCT.

En-face OCT imaging requires movement of at least one of the transverse scanners in a 2D scanner assembly faster than the scanner performing the depth scanning. To generate a raster looking image, the en-face OCT employs a fast transverse scanner and a slow transverse scanner, both operating faster than the scanner performing the depth scanning. In order to adjust the reference path length, in the papers and patents mentioned above, mirrors are used which are translated by mechanical means. This is characterized by the disadvantage that the signal has to be extracted from single mode optical fiber and reinjected back into the same or a different single mode optical fiber. This procedure introduces losses and requires specialized high accuracy and high mechanical stability 3D stages for launching light into a single mode fiber. In a series assembly line in a factory, such a configuration would require significant assembly time and the final product would be expensive.

Therefore, using an all fiber reference path would be advantageous. An all fiber configuration is disclosed in the U.S. Pat. No. 6,201,608B1. However, this disclosure employs a specialized light source which operates in regime of amplification for the signal returned from the target. Two optical paths in fiber are constructed in combination with the specialized optical source. In this case, the depth scanning is achieved by moving a stage supporting a group of elements towards and backwards from the object. The elements grouped on the moving stage are the transverse scanner and the interface optics only.

Such a grouping and assembly has the added disadvantage that a fiber loop is required to connect the stage with the rest of the OCT system. When the stage moves, vibrations are induced in the fiber loop which leads to noise. Also, the polarization of the light propagating down the fiber link may change due to the alteration in the spatial distribution of radiation within the fiber cord, which leads to reduction in the visibility and signal to noise ratio. Such a solution requires an expensive light source and expensive polarization maintaining fiber in order to avoid noise generation in the fiber and changes in the polarization due to fiber cord being shaped during the depth scanning.

Additionally, as shown in the paper by T. Sawatari mentioned above, in order to generate an interference image in the heterodyne scanning microscopy, a phase or frequency modulator is required to create a bit signal, or a carrier for the image signal. The embodiments in the U.S. Pat. No. 6,201, 608B1a use such phase moduostors. Such modulator is expensive, ads losses, reduces the efficiency in using the signal and introduces dispersion which deteriorates the depth sampling profile of the OCT.

As another disadvantage, during the stage movement, the focus position slips away from the coherence gate position, given by the point in the volume of the object, where the optical path difference in the interferometer is zero. The longer the depth scanning, the larger the difference between the focus and the coherence gate point, with disadvantageous reduction in the signal strength.

Signal strength and transverse resolution depend on how well the focus is matched to the coherence position (wherein tracking of the focusing and zero optical path difference are referred to as dynamic focus). Dynamic focus was described in PCT patent publication No. WO 92/19930, but only in principle. Possible optical configurations to simultaneously scan the depth and the position of the focus in the depth are described in U.S. Pat. No. 4,589,773, in U.S. Pat. No. 6,057, 920 and in U.S. Pat. No. 6,144,449. These solutions however, require mechanical synchronism of elements or adjustment of ratios of focal lenses or movement of a bubble elastic lens respectively, with the consequence limitation in speed.

Another method was described in the paper "An optical coherence microscope with enhanced resolving power in thick tissue", by J. Schmitt, S. L. Lee and K. M. Yung, published in Optics Communications, 142, (1997), pp. 203-207 where the focusing lens in the object arm was synchronously moved with retroreflectors in the reference arm. In this way, for a movement of the objective lens towards the tissue by x, the OPD varies by $2n^2x-4$, where n is an average value for the index of refraction of the medium. When $n^2$ is approximately 2, which happens for most of the tissue structures, then OPD is approximately zero and dynamic focus is automatically accomplished. However, the method uses a mirror which redirects high power to the optical source, and it is known that low coherence source are prone to noise in the presence of feedback. The movement employs elements in both object and reference arm which makes the method cumbersome to implement. Another method for dynamic focus applicable for the case when $n^2$ is approximately 2 is disclosed in the patent WO 02/04884. This last disclosure presents a simultaneous movement of a lens and of a beam-splitter separating the reference and the object beams in the interferometer. This requires stable mechanical fixtures, low vibrations and the method cannot be implemented in fiber version.

The dynamic focus methods described above are devised especially for longitudinal OCT, where B-scan images are generated by fast scanning along the depth coordinate with a slower scanning along a transverse coordinate. As such, the method needs to be fast, and operational at the depth scanning rate of, for example, a rate on the order of 100-1000 Hz.

The U.S. Pat. No. 6,201,608B1 provides for solutions for dynamic focus to maintain the coherence gate in synchronism with the focus dedicated for microscopy. The solutions presented are restricted to high numerical aperture values, 0.4 to 1.5, as required by microscopy applications of imaging small objects. Even if no dynamic focus is applied, if the specimen thickness is small, such as the case in microscopy, scanning the depth using a translation stage as that described in FIG. 8*a* is feasible. However, a system using the implementation in FIG. 8*a* cannot be used to image large curved objects which require axial scans much larger than the thickness of the tissue investigated. A typical example is that of the cornea, which has 0.5 mm thickness, but axial scanning has to cover 5 mm to 10 mm. Such an object to be imaged requires a solution of dynamic focus. The U.S. Pat. No. 6,201,608B1 does not show how such large objects could be imaged by moving a stage with the scanner and the interface optics axially to and back from the object. As another problem when imaging the cornea is the high signal reflected from the epithelium with diminished brightness for the scatterrers from inside the cornea tissue. In many imaging applications the exact ratio of brightness from different pixels is less important as to collect sufficient signal image to display the morphology from deep in the tissue. If dynamic focus was applied to the cornea, then the high signal from the epithelium may saturate the electronics circuitry.

Thus, a need exists for a better procedure of implementing the depth scanning and processing of the OCT signal. In particular, in the first instance, a better configuration less susceptible to noise and which does not alter the polarization state would be desirable. Secondly, a procedure having improved efficiency in using the signal and tolerant to dispersion would be advantageous. Thirdly, a procedure to implement axial scanning by moving the transverse scanner and the interface optics to obtain sufficient signal collection from large and curved objects without dynamic focus. Fourthly, a solution for dynamic focus to maintain at least partially, the synchronism between the focus and the coherence gate points during the depth scanning would be desirable.

Accordingly, the present invention provides for improvements over at least one of the problems of the prior art as stated hereinabove, or as described herein below.

SUMMARY OF THE INVENTION

In one aspect the invention provides a method for adjusting the focus in an optical coherence tomography (OCT) apparatus destined for imaging large curved objects in order to improve the signal strength and transverse resolution. The OCT apparatus comprises an optical source, an interferometer generating an object beam and a reference beam, and in the object arm, optical fiber connection towards a focus element, a transverse scanner and interface optics for scanning an object with said object beam, and a processor for generating an OCT image from an OCT signal returned by said interferometer, and wherein at least said fiber connection, focus element, scanner and interface optics are mounted on a common translation stage displaceable towards and away from said object. By conveniently adjusting the focus element depending on the curvature of the object, the error between the depth position of the best focus and that of the point sampled by the coherence gate during transverse and axial scanning is diminished.

In another, aspect the invention provides an optical coherence tomography (OCT) apparatus comprising an optical source, an interferometer generating an object beam and a reference beam, and in the object arm, optical fiber connection towards a focus element, a scanner and interface optics for scanning an object, and a processor for generating an OCT image from an OCT signal returned by said interferometer, and wherein at least said optical source, said interferometer, and said scanner are mounted on a common translation stage displaceable towards and away from said object and the focus is adjusted according to the method mentioned in the first aspect above.

According to another aspect, the present invention provides an optical mapping apparatus which in a preferred embodiment, comprises an optical radiation source which is divided into an object beam along an object arm and a reference beam along a reference arm starting at the respective $1^{st}$ output and $2^{nd}$ output of a first optical splitter; where light from the $1^{st}$ output of the first optical splitter is sent to an input port 1 of a second optical splitter and the light at one of the corresponding output port, 2, of the second optical splitter is sent via a focusing element towards a transverse scanning means and the port 3 of the second optical splitter, where light traveling from the transverse scanning means toward the port 2 appears, is optically connected to the $1^{st}$ input of a third optical splitter and where the $2^{nd}$ input of the third optical splitter receives light from the $2^{nd}$ output of the first optical splitter via a delay line; where the said transverse scanning means effect 2D transverse scanning of an optical output from the second optical splitter, over a line or a predetermined area in an object to be investigated or imaged, transverse scanning means preferably consisting of a line scanner and a frame scanner; interface optics for transferring an optical beam from the transverse scanning means to the object and for transferring an optical output beam reflected and scattered from the object back to transverse scanning means, and therefrom to the second optical splitter; focusing means, which together with the interface optics means act to project a focused spot on the target or inside the volume of the object investigated; optionally, when the object is the eye, a fixation lamp unit, interleaved with the interface optics, for sending light towards the eye for guidance; balanced photodetector unit which receives light from the two outputs of the third splitter; analyzing means for processing the signal delivered by the balanced photodetector unit; optionally, the focusing means are synchronously adjusted with the movement of the translation stage to implement dynamic focus, i.e. to maintain the point of OPD=0 in the focus; displaying means for processing and generating an image created by the analysing means, which image is synchronised with the transverse scanning means; and where the reference path is defined as the path taken by the reference beam from the first splitter up to the third splitter and the object path is defined as the path taken by the object beam from the first splitter, via the second splitter, focusing element, transverse scanning means, interface optics up to a depth inside the object to be investigated and therefrom back via the interface optics, transverse scanning means, focusing element towards the second splitter up to the third splitter and the delay line is adjusted to match the optical length of the reference path to the length of the object path; at least a polarization controller to match the orientation of the polarization in the object and reference paths; translation stage which supports the three optical splitters, the polarization controller or controllers, the optical radiation source, the focusing means, the transverse scanning means and the interface optics, the optional fixation lamp, the optional adjustment means of the focus, stage which can be controlled to move towards and backwards from the object and all connections from the stage to the rest of the optical mapping apparatus are in the form of elastic electrical cables only. In this way, profilometry of corrugated surfaces or curved surfaces such as cornea is accomplished by simultaneously maintaining the coherence gate in the focus.

Embodiments of the invention solve the above discussed problems and relate to an apparatus wherein the fiber leads are not stretched during the depth scanning.

In another embodiment the invention provides a method and apparatus to encode the reflectivity of the backscattered signal with no increase in the dispersion and signal loss.

In a yet another embodiment the invention provides a method and apparatus for dynamic focus.

Overall, the invention sets out a simplified, low cost configuration easy to be assembled in series in a factory, in a very compact format.

In preferred embodiments, the second optical splitter is either a two by two optical splitter, or an optical circulator.

In a preferred embodiment, the three optical splitters and the delay line are implemented all in single mode fiber. In this case, in order to optimize the signal to noise ratio, an in-fiber attenuator is used in the form of a connector between connectors connecting the first and the third splitter.

In a preferred embodiment, when the second optical splitter is a two by two optical splitter, the said first splitter is eliminated, the optic source is connected direct to the second splitter and the reference path is connected to one output of the second splitter.

In a preferred embodiment, a supplementary optical splitter is incorporated either between the output of the second optical splitter and the focusing means or between the second and the third optical splitter in order to divert some of the light backscattered by the object towards a confocal receiver. This splitter is termed in what follows as a confocal optical splitter. In this case, the analyzing means process simultaneously two signals, one delivered by the balanced detection unit and the other by the confocal receiver and the displaying means display simultaneously two images, OCT and confocal respectively.

In another embodiment, the optical source is made of two sources, a first low coherence source to generate the OCT image and a second optical source, whose wavelength is advantageously chosen to maximize the sensitivity of the photodetector used in the confocal receiver unit.

The optical radiation source is preferably a low coherence source, or a source with adjustable coherence length.

All embodiments of the present invention can operate in at least one of the following regimes of operation: A-scan, T, B, C-scan or 3D.

In the A-scanning regime, the transverse scanning means are fixed, deflecting the object beam to a fixed desired angular or lateral inclination, the translation stage is used to explore the depth range and the mapping apparatus acquires an A-scan, i.e. a one dimensional reflectivity profiles in depth and in the embodiments of the apparatus equipped with a confocal receiver, the apparatus according to the invention acquires simultaneously a one dimensional reflectivity profile in depth in the OCT channel and a one dimensional reflectivity profile in depth in the confocal channel.

In the T-scan regime, the transverse scanning means are used to move the object beam angularly or laterally in a time $T_H$ along a prescribed contour, which could be a horizontal line, a vertical line, a circular path, an elliptic path or any other open or closed path, while the translation stage is at rest, and a one dimensional en-face profile of the reflectivity versus the transverse position is obtained. In the embodiments of the apparatus equipped with a confocal receiver, the apparatus according to the invention acquires simultaneously a one dimensional en-face profile of the reflectivity versus the transverse position in the OCT channel and a one dimensional en-face profile of the reflectivity versus the transverse position in the confocal channel.

In the B-scan regime, the said translation stage is moved in steps after each T-scan to cover the depth range in a number of steps which determines the number of lines in the image frame, or the said translation stage is moved continuously in a time $T_B > T_H$ where the number of lines in the image frame is $T_B/T_H$, generating in this way a two dimensional map of reflectivity as a cross section through the object in a surface containing the optic axis and the T-scan contour.

In the C-scan regime, the transverse scanning means are used to move the beam angularly or laterally to cover a two dimensional pattern describing different shapes of T-scans in a time $T_C$ while the translation stage is kept fixed to generate a 2D map of reflectivity for constant depth in the reference path of the interferometer.

In the 3D-scan regime, the translation stage is moved in small steps after each C-scan to cover a depth range or at a constant speed less than the ratio determined by dividing the depth resolution to $T_C$, covering the depth range in a time $T_{3D}$ and a number $T_{3D}/T_C$ of C-scans are stored and then used to generate a 3D image of the interior of the object.

In order to implement a compact apparatus configuration, no external phase modulator is employed for creating the carrier of the OCT signal. This allows the reference path to be continuous in optical fiber, for low losses and high mechanical stability. Therefore, in the T-scan, B-scan or C-scan regimes of operation, the signal is encoded based on the phase modulation only, created by the movement of the transverse scanning means along the T-scan direction which determines the line in the raster of the B-scan or C-scan image, movement which determines modulation of the interference signal.

BRIEF DESCRIPTION OF THE DRAWINGS

The invention will now be described in more detail, by way of example only, with reference to the accompanying drawings, in which:

FIG. 1a to 1c show, in diagrammatic form, the error between the focus surface and the coherence gate surface for a flat object.

FIG. 9 shows, in diagrammatic form, two possible embodiments for the second optical splitter.

FIG. 10 shows, in diagrammatic form a different layout for the second and third optical splitter.

FIG. 11 shows, in diagrammatic form a different layout for the second and third optical splitter, similar to that in FIG. 8 but incorporating an optical splitter for the confocal receiver.

DETAILED DESCRIPTION OF THE PREFERRED EMBODIMENTS

Figure 1B:
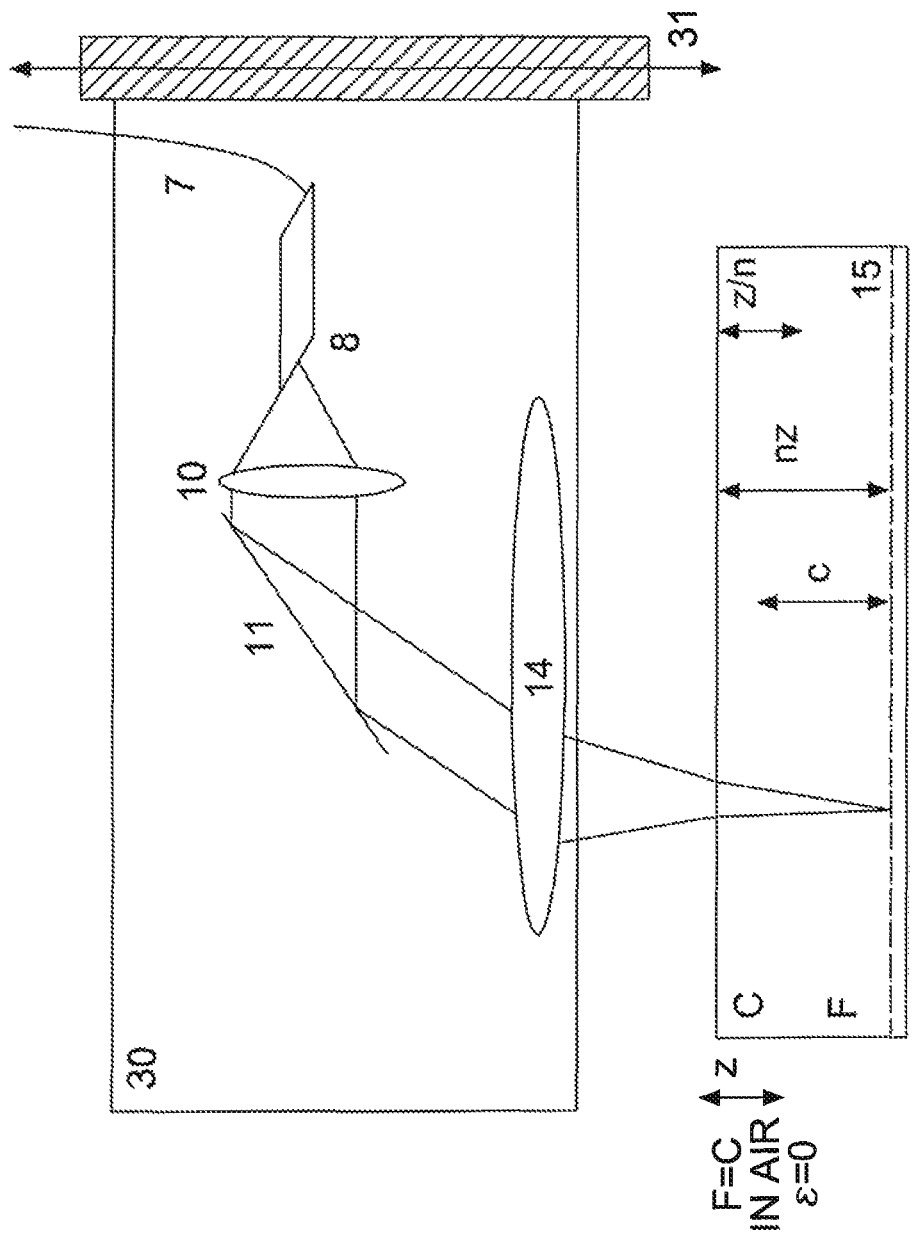

Various features of the present invention, as well as other objects and advantages attendant thereto, are set forth in the following description and the accompanying drawings in which like reference numerals depict like elements.

An OCT device may involve and make use of techniques known in the art and described in GB patent (Younguist Davies) no. 8611055; U.S. Pat. No. 5,459,570, U.S. Pat. No. 5,321,501, U.S. Pat. No. 5,491,524, U.S. Pat. No. 5,493,109, U.S. Pat. No. 5,365,335, U.S. Pat. No. 5,268,738, and U.S. Pat. Nos. 5,644,642 and 5,975,697 (Podoleanu), which are herein incorporated by reference. These devices can be constructed in bulk or optical fiber, and have means for transversally scanning the target, means for longitudinal scanning of the reference path length, means for phase modulation, means for controlling the polarization stage as bulk or fiber polarizer controllers, and have means for compensating for dispersion. In embodiments of the present invention, no phase modulator is required and because all the reference path is in fiber, the embodiments exhibit dispersion, which in accordance with the embodiments of the invention can be tolerated if proper wavelength is used, such as 1300 nm.

FIG. 1 diagrammatically shows elements of the object arm to be used in the disclosure to illustrate how different elements influence the axial position of the focus surface and coherence gate surface. Light from fiber 7, emerges from the fiber end, 8, cut at an angle or equipped with a FC/APC connector. A focus element 10, shown in the form of a lens, changes the convexity of the wavefront of the beam emerging from the fiber end 8, beam which is subsequently sent to the transverse scanner 11. For simplicity, only one galvo-scanner mirror is shown, however a 2D transverse scanner could equally be employed in FIG. 1, or two galvo-scanners separated by lenses or mirrors according to means known in the art. The interface optics 14 transfers the fan of rays from the transverse scanner 11 to scanning beams which converge on the surface F. If only one galvo-scanner is used in FIG. 1 then the surface where the beams are focused becomes a line. In FIG. 1, the interface optics 14 uses a lens, however mirrors or several lenses could be used, or such optical elements, lenses or mirrors are interleaved with the two transverse scanners to achieve raster scanning. However, the conclusions drawn from the simplified configuration in FIG. 1 are valid for such more complex scanning configurations. In FIG. 1, focus element 10 collimates the beam incident on the transverse scanner 11. By placing the scanner 11 at f from the lens 14 of focal length f, the focus surface, F, is at f away from the lens 14.

In practice, by moving the lens 10 axially, the focus surface F can be moved closer or away from lens 14, i.e. to values different from f, as illustrated in FIG. 1a. The elements in FIG. 1 are common to all embodiments to follow. They are incorporated into the object arm of the OCT interferometer. By altering the path difference between the length of the object arm and the length of the reference arm, the coherence gate surface, C, is moved axially. Ideally, the surface C should coincide with the surface F for maximum signal returned to the OCT interferometer.

If the object 15 is planar, or if the surface facing the lens 14 is flat, then the two surfaces, F and C will always be parallel to each other when actuating on the focus element 10. If all elements in FIG. 1 are placed on a common stage, 30, moved by a translation stage 31, axially, towards and away from the object 15, then the two surfaces F and C are moved together. However, depending on the depth in the object 15 and on its index of refraction, the two surfaces are separated by a variable error, $\epsilon$. Such objects could be in the form of a flat glass block or biology specimens, or histology samples, with little height variations in comparison with their lateral size.

Let us consider that initially, the error $\epsilon$ is zero (i.e. the two surfaces F and C coincide) in air, position shown by F=C in FIG. 1b. For a depth z, the focus is pushed further inside to zn while the coherence point selected by OCT is pushed backwards to z/n. The error is $$\epsilon = zn - z/n \quad (1a)$$

Figure 1C:
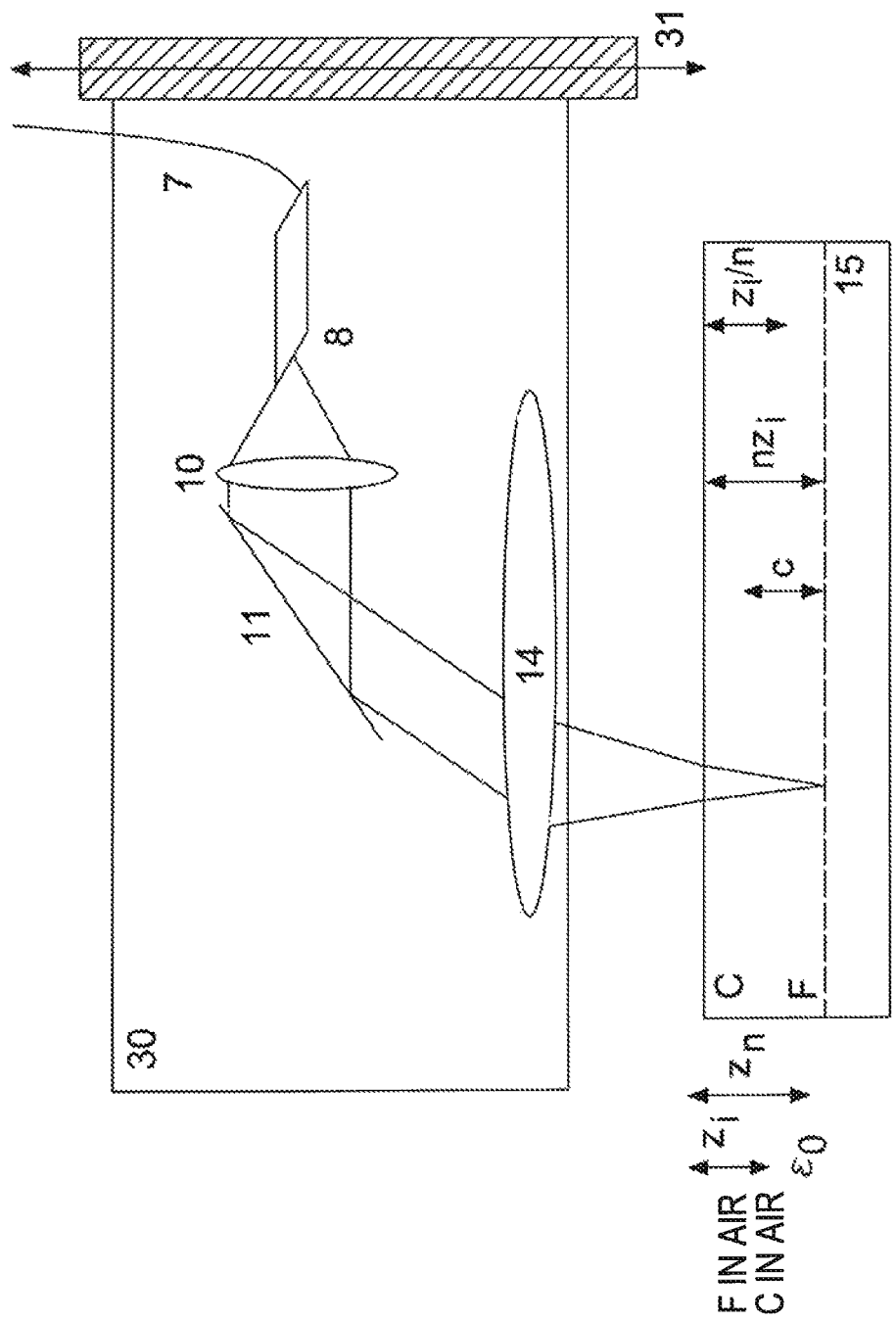

In case that the error $\epsilon$ is set deliberately to a value different from zero in air, then at a certain depth inside the object, the error $\epsilon$ is brought to zero. To illustrate this case, let us say that in air, the focus line, F, is closer to the lens 14 than the confocal line, C, as shown in FIG. 1c. By moving the stage 30, towards the object 15, when both lines are inside the object 15, the axial distance between the front surface and the initial focus position is $z_f$ and the axial distance between the front surface and the initial coherence position is $z_c$. Then the error is $$\epsilon = z_f n - z_c/n \quad (2a),$$

This could be brought to zero when:

$$z_f = z_c/n^2 \quad (3a)$$

Considering $z_f = z$, $$\text{then } z_c = z + \epsilon_0. \quad (4a)$$

Using (4), equation (3) becomes:

$$z_0 = \epsilon_0/(n^2 - 1) \quad (5)$$

The error varies between:

$\epsilon = -\epsilon_0$, when the stage is moved up to the front surface of object 15 to coincide with the coherence gate surface, C.

to $\epsilon = 0$, when the stage is moved closer to the object 15, when $$z_0 = \epsilon_0/(n^2 - 1) \quad (6)$$

and to:

$$\epsilon = (n - 1/n)t - \epsilon_0/n \quad (7)$$

when the stage is moved to place the focus surface on the bottom object surface, which marks the object thickness, t.

The paragraph above shows that without dynamic focus, by a careful adjustment of the initial error $\epsilon_0$, it is possible to minimize advantageously the range of errors $\epsilon$ inside the object 15 when scanning the object in depth by moving the stage 30 towards the object. Even more, taking into account that the interface air—object usually determines the maximum peak in the distribution of reflectivities in depth, it is desirable to reduce the peak corresponding to the first interface by increasing the error $\epsilon$ when the coherence surface coincides with the front surface, while at the same time, moving the synchro depth $z_0$ deeper into the tissue, wherefrom the signal strength is usually smaller.

Because the object is flat, the error is the same along the points situated on a T-scan line. In the following we demonstrate that the same method could be advantageously combined with the curvature of the investigated object, such as the cornea or craters, to minimize the error in chosen points along the T-scan inside the object.

FIG. 1c also shows in schematic form the remaining part of the interferometer 50 and the processor 51 for processing the signal from the interferometer to produce an image.

Figure 2A:
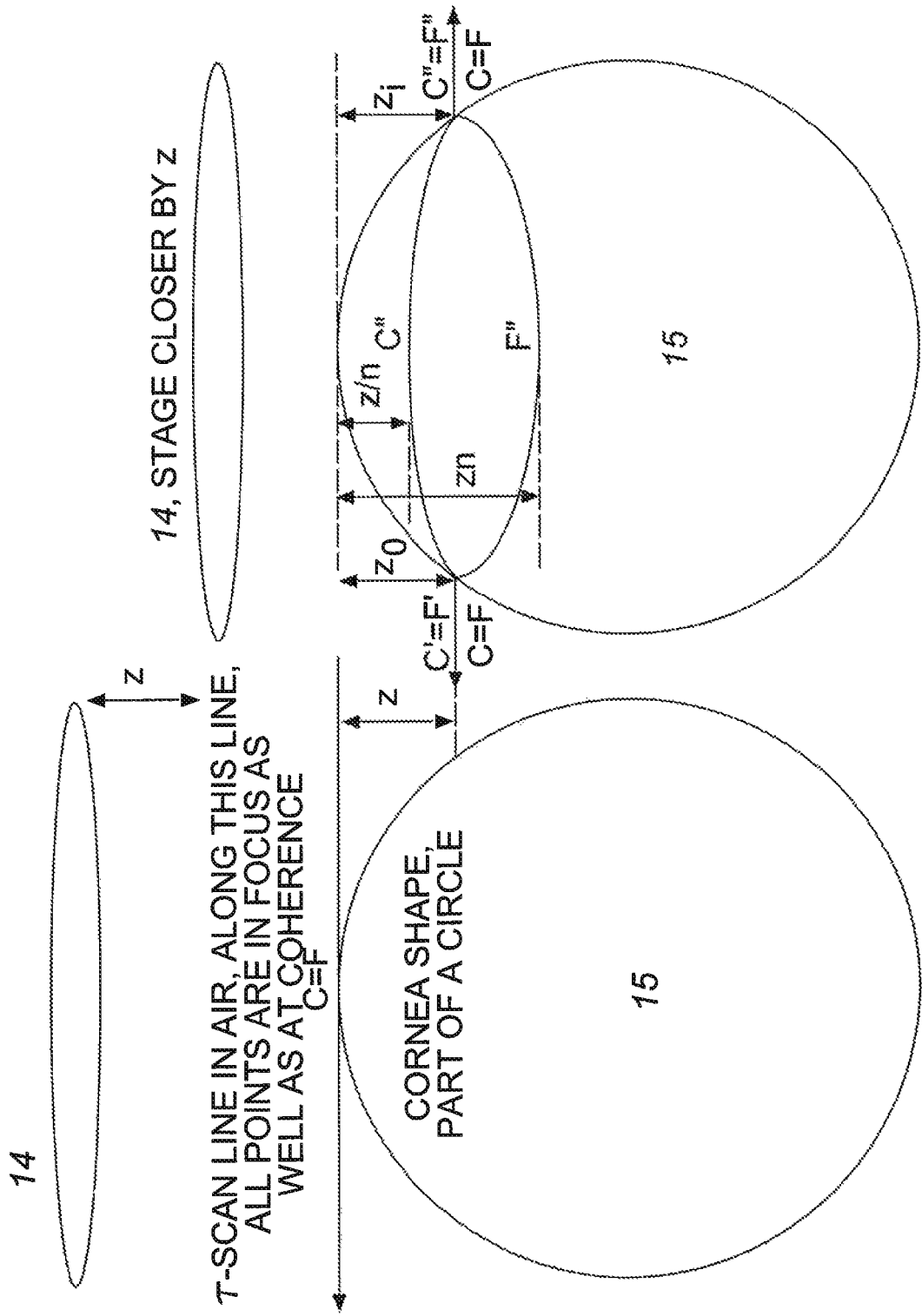
FIGS. 2a to 2c shows, in diagrammatic form, the error between the focus surface and the coherence gate surface for different shapes of curved objects.

FIG. 2a left shows the two surfaces, C and F coinciding, where the distance to the object 15 is such as the T-scan just touches its top.

FIG. 2a right shows how the two surfaces evolve differently inside the object, after the stage 30 was moved closer to the object 15 by a distance z. The two surfaces, C and F bulge in and out respectively, due to the object curvature. In opposition to the case of the flat object 15 in FIG. 1, where the two surfaces, C and F are parallel to each other, here they are curved. The error varies along the T-scan line, from zero in the points C'=F' on the object border to a maximum in the center, as measured by the distance between C''' and F''':

$$\epsilon = zn - z/n \quad (1b)$$

Figure 2B:
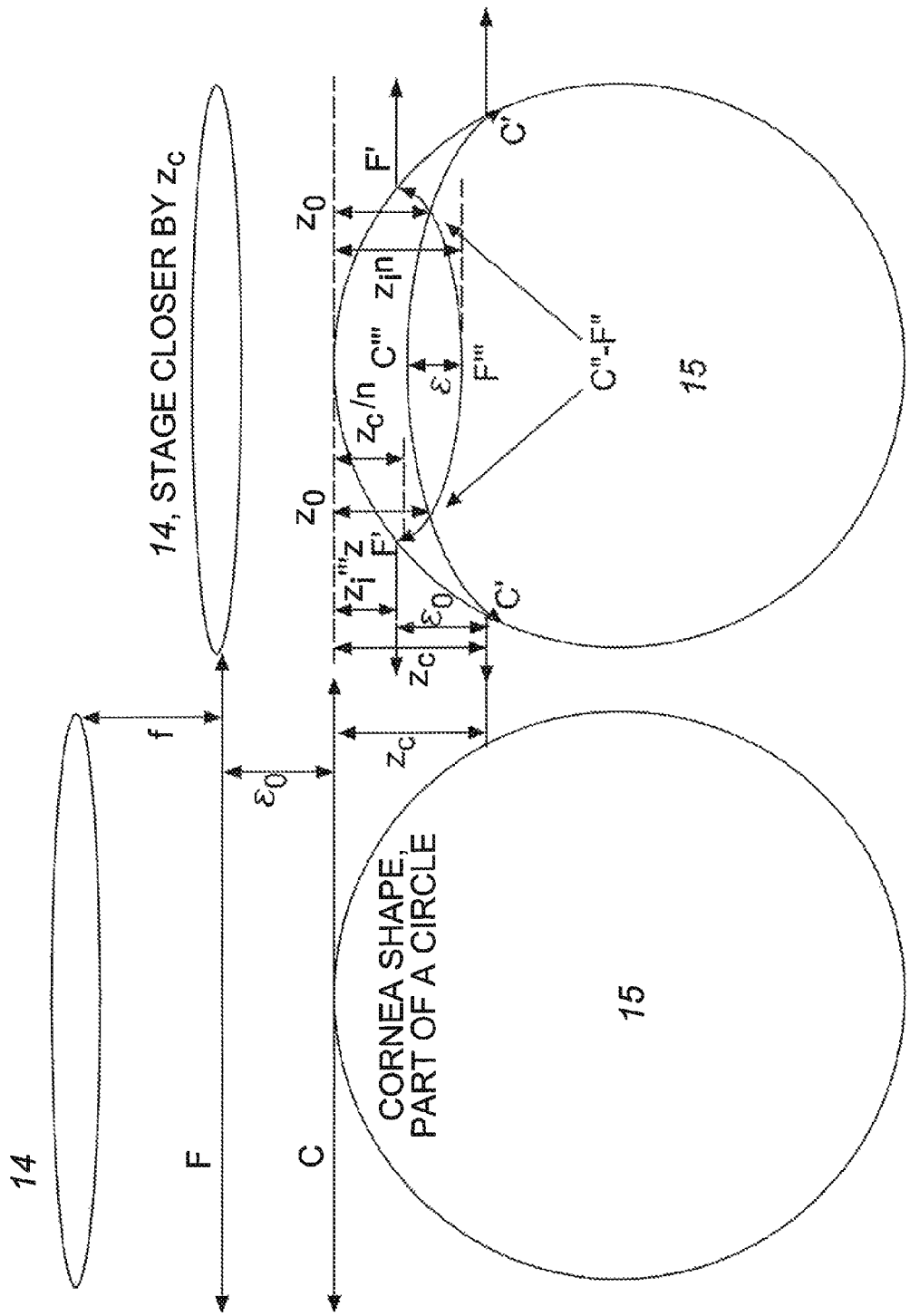

FIG. 2b shows a different case, where the two surfaces C and F are deliberately made to differ by $\epsilon_0$, as an example of implementation of the method according to the invention. In opposition to the case in FIG. 1, the error varies from $\epsilon = -\epsilon_0$, in the point C' situated on the object border, to a maximum as measured between the points C''' and F''':

$$\epsilon = z_f n - z_c/n \quad (2b)$$

This could be brought to $\epsilon = 0$ when:

$$z_f = z_c/n^2. \quad (3b)$$

Considering $z_f = z$, then $z_c = z + \epsilon_0$. \quad (4b)

Using 4b, 3b becomes:

$$z_0 = \epsilon_0/(n^2 - 1)$$

in points C''=F''

For instance, a possibility to implement the method according to the invention is to halve the error at the thickness of the cornea in comparison to the case in FIG. 2a. In the case of the human cornea, the thickness is 0.5 mm. If the two surface, C and F were superposed in air like in FIG. 2a, then at 0.5 mm inside the anterior chamber with an index of refraction n=1.4, a maximum error of $\epsilon_M$=343 μm results.

Using the method according to the invention, we could halve this error along the T-scan when C''' is at the bottom of the cornea. C''' corresponds to $z_c/n$=thickness t=0.5 mm. If we are after a half value of the error, 0.171 μm, then $$z_f n = z_c/n + 0.175 = 0.675, \text{ this gives:}$$

$$z_f = 0.482 \text{ and } \epsilon_0 = 0.218.$$

For such adjustment, the error along the surface C varies from −0.175 μm in C' to 0 in C'' and then to 0.175 μm in C'''. In other words, along the T-scan sampled by the OCT, the range is $[-\epsilon_M/2, \epsilon_M/2]$, while in FIG. 2a, is in the range $[0, \epsilon_M]$.

Such an adjustment was made possible by introducing an error in air $\epsilon_0$ in such a way that the focus surface, F, is closer to the interface optics 14 and stage 30 than the coherence gate surface, C.

Figure 2C:
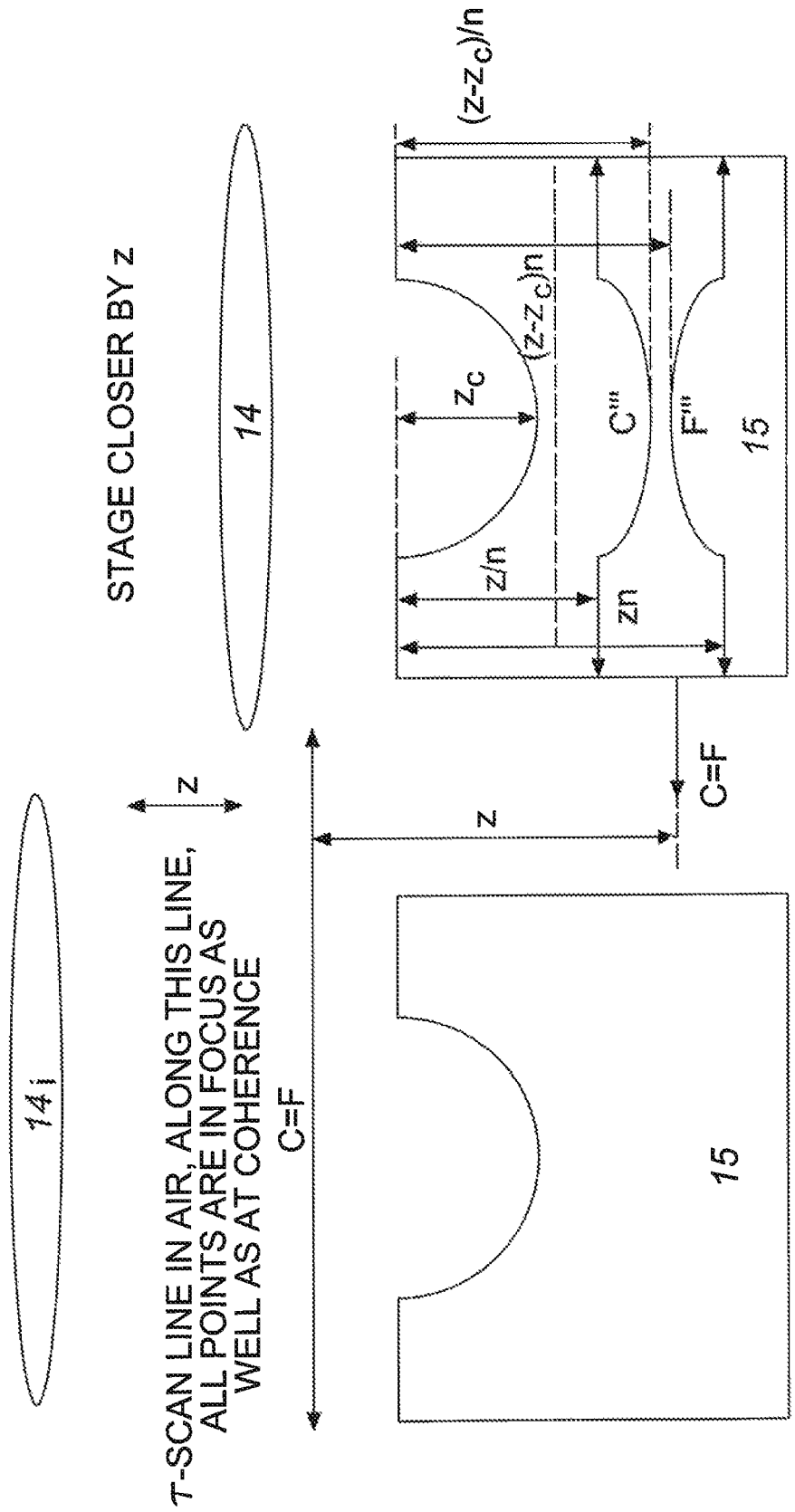

FIG. 2c shows an object where the object curves away from the stage 30. This is a spherical shaped crater in a block of scattering transparent material for instance. In this case, below the curved front surface, the focus surface bulges out and the focus surface bulges in, in opposition to the bulging directions of the respective surfaces in FIGS. 2a and 2b. Obviously, as in FIG. 2b, the two surfaces C and F can be made to intersect each other by introducing an error $\epsilon_0$ in air. However, in opposition to the object in the case in FIG. 2b, where the F surface was placed closer to the stage 30, the C surface has to be moved closer to the stage 30 for the object in FIG. 2c in order to make the two surfaces, C and F coincide within the object volume below the shown spherical shaped crater.

The two cases in FIG. 2a, b one hand and in FIG. 2c on the other demonstrates that the optimum adjustment of the focus element depends on the object shape.

Figure 3:
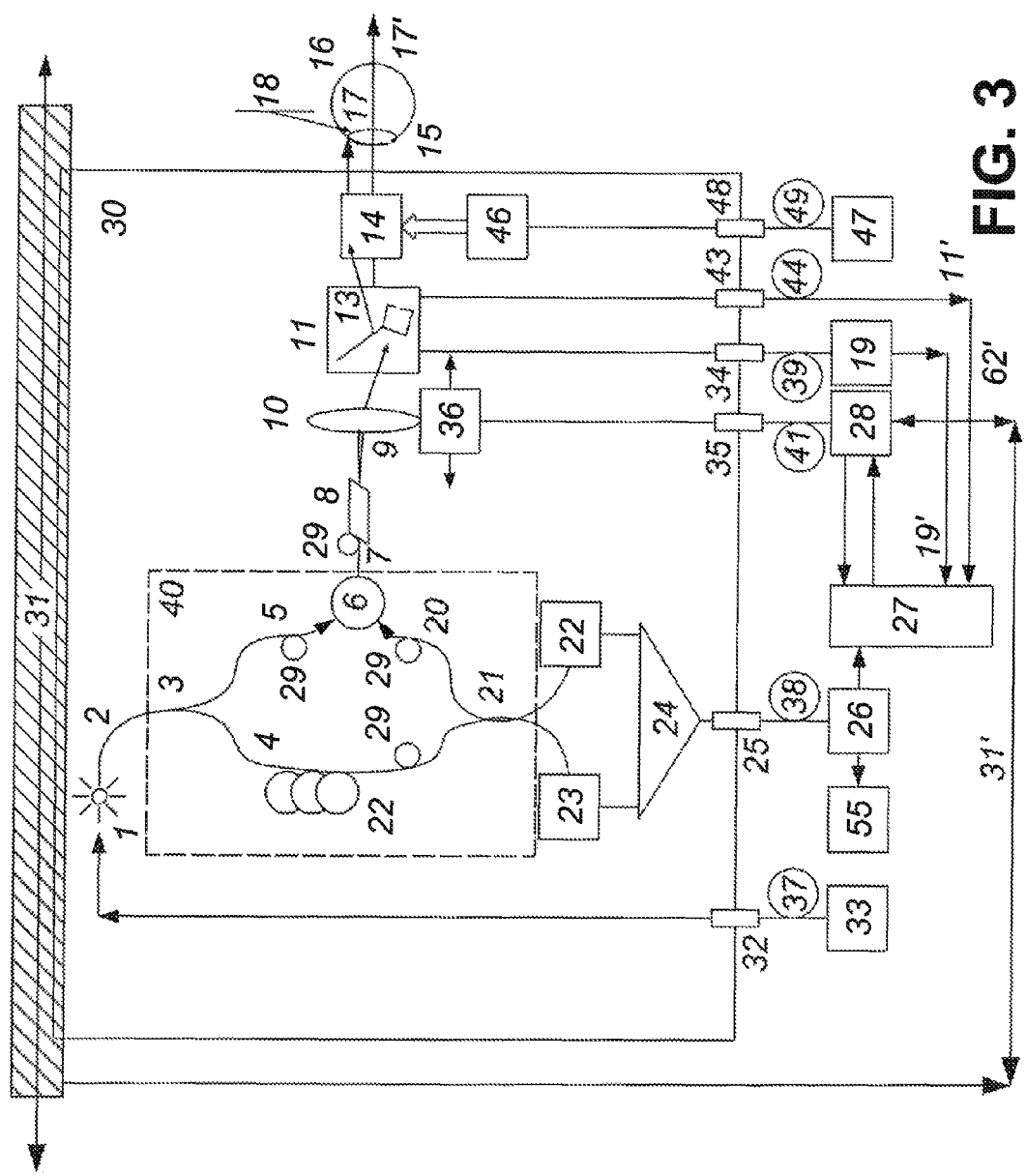
FIG. 3 shows, in diagrammatic form, a first embodiment of the compact high resolution mapping apparatus providing an OCT image.

FIG. 3 diagrammatically shows the embodiment of a compact OCT apparatus according to the invention. The apparatus comprises an optical source, 1, which can be either low coherence or with adjustable coherence length, pigtailed to a single mode fiber, 2, wherefrom the power is split in a first optical splitter, which in FIG. 3 is shown as a directional single mode coupler, 3, into a reference beam, along the reference path 4 and an object beam, along the object path, 5. Light into the object path 5 is launched from the 1$^{st}$ output of the first splitter and light into the reference path 4 is launched from the second output of the first splitter.

In the context of the invention, a low coherence source is a broadband source, whose coherence length is much less than the penetration depth of the radiation used in the object studied. Examples of such sources include superluminiscent diodes, tungsten lamps, Kerr-lens mode-locked lasers, laser diodes below threshold and diverse combinations of the above. For instance, at the level of the technology today, the coherence length of such sources cover the range of 0.5-500 µm. In contrast, in the context of the invention, a high coherence source has a coherence length much larger than the penetration depth of the radiation used in the object studied. Examples of such sources include lasers, with a coherence length larger than 1 cm.

In the object path, a second optical splitter, 6, which in FIG. 1 is shown as an in-fiber circulator, is used to transfer light from the 1$^{st}$ output of the first optical splitter and send light, via path 7 to output 8, terminated with a fiber connector at an angle, or cleaved at an angle, to minimize the fiber end reflection and in this way the noise. From the output 8, the light is sent via free space, 9, towards the focusing element 10, such as a refractive or reflective optical element and then deflected by a 2D scanner head 11, equipped with mirrors 12 and 13 to scan transversally, via interface optics 14, an object.

In FIG. 3 the object is either the cornea, 15 or the retina, 16, of an eye 17, in which case the beam is focused by the cornea 15 and eye lens 18 onto the retina 16. The object could be any other type of tissue or industrial object, such as powder or lenses to be tested, such object being placed where cornea 15 or the retina 16 are shown in FIG. 1. The line connecting the transverse scanning means and the object constitutes an optic axis of the apparatus, oriented along the deflected object beam in the middle of the scanning range of the transverse scanning means.

Scanner head 11 is a scanning assembly means known in the art and includes, for example, galvanometer scanners, piezo-vibrators, polygon minors, resonant scanners, acousto-optic modulators, rotating or vibrating prisms etc. Combinations of scanners from the list above can be used for the scanning pair head 11. One scanner usually works fast and the signal collected during its movement is displayed on the line in the raster of the final image, termed as the line scanner, while the other scanner, is typically termed as frame scanner. For instance, a polygon mirror can be used as the line scanner and a galvanometer scanner can be used as the frame scanner. The scanner head 11 is under the control of triangle, saw-tooth or DC voltages produced by a generator 19.

The scanning head 11 can be divided in two parts, namely the line scanner and the frame scanner, separated by optical elements like lenses and/or mirrors in configurations known in the art of scanning laser ophthalmoscopes (SLO) aand of confocal microscopy or general raster scanning systems, in which case the scanner head 11 and interface optics 14 are interleaved to each other, in one block, and only for convenience are they represented here separately. The scanner mirrors, 12 and 13, which refer to either galvanometer scanners or polygon mirrors have high reflectivity at the wavelength used, or if acousto-optic modulators are used, their transmission at the wavelength used is high. By means known in the art, the two scanners have orthogonal axes or scan the ray in perpendicular planes, producing a raster in the plane (X,Y), oriented perpendicular on the optic axis of the system. Circular scan, (ρ,θ) of the ray can also be obtained by sinusoidally scanning the ray using the two scanners in orthogonal directions at the same frequency with a phase difference of π/2, where ρ is determined by the amplitude of the angular deviation, measured in a plane perpendicular on the optic axis from the point hit by the ray when the scanners are not driven, and θ is a polar angle in this same plane.

Light returned from the object, via the interface optics 14, and then via the scanning head 11, is launched via the focusing elements 10 back into the second optical splitter 6, i.e. into the same port fiber, 7 of the circulator, 6, where the light originated from. The circulator routes the signal to the fiber output 20, which takes the signal to a first input of a third optical splitter 21, which in FIG. 3 is shown as a single mode directional coupler. The second input of the optical splitter 21 receives light from the reference path, 4, via a fiber delay line 4'. The object signal interferes with the reference signal when the optical path difference (OPD) between the reference path length and the object path length is less than the coherence length of the source 1. This explains the selection in depth of the OCT. The reference path starts at the optical splitter 3 and ends at the optical splitter 21, and is made of fiber 4 and delay line 4'. The object path starts from the optical splitter 3 and again ends on the optical splitter 21, made out of fiber 5, circulator 6, fiber 7, fiber connector 8, free space path 9, focusing element 10, scanner head 11, interface optics 14 up to the object and back to the fiber 7. Points along the object beam in the volume of the object will contribute to the signal only from within the coherence length of the source in the volume of the object. The disclosure in FIG. 3 has the advantage that the reference beam is all in fiber and no losses or vibration induced noise are incurred due to passing the light from fiber to free air and back, to allow for the adjustment of the reference path length. The OPD is adjusted instead on the expense of the object path length only. Such a configuration requires less assembly time, essential in series production. As fiber length compensates for the path in air in FIG. 1, dispersion may exist which may enlarge the depth sampling profile of the apparatus. However, it is known that single mode fiber at 1300 exhibits little dispersion. Because there is no loss in the reference arm, excess photon noise may be large, and in order to maximize the signal to noise ratio, attenuation of reference path is required. In this case, such attenuation can be obtained by introducing an adaptor between FC/APC connectors, where the mating of the two connectors in the reference arm, such as the two tilted connectors bringing fiber from the first or the second splitter towards the connector of the third splitter, are set at different angles in between. In this way, by changing the adaptor, which has different slits for the two FC/APC connectors, different attenuation can be introduced, at a set value dependent on the relative rotation orientation of the two FC/APC or FC/ST or other types of connectors known in the art.

To maximize the interference signal, polarization of light in the two arms of the interferometer needs to be the same. Therefore, at least a polarization controller 29 in one of the object path or reference path is required.

The optical splitter 21 is terminated on two photodetectors 22, 23 of a balanced photoreceiver unit 24. Preferably the splitter 21 needs to be an even 50/50 splitter for the whole band of wavelengths used, in order to achieve suitable reduction of the intensity noise and excess photon noise characteristic for low coherence sources. The photodetected signal obtained at the electrical connector output, 25, of the unit 24 is sent to the processing block 26 to provide strength proportional to the reflectivity, or the log version of the reflectivity, and then displayed and recorded by means of a suitable display device 27, such as a frame grabber, a storage oscilloscope or a suitable printer. The device 27 is under the control of computer 28. The block 26 contains a band pass filter followed by a rectifier and a low pass filter.

The filter is adjusted on two different functions depending on the regime of operation of the apparatus, as described below.

In the T-scan regime, the transverse scanning means are used to move the object beam angularly or laterally in a time $T_H$ along a prescribed contour, which could be a horizontal line, a vertical line, a circular path, an elliptic path or any other open or closed path, while the translation stage is at rest, and a one dimensional en-face profile of the reflectivity versus the transverse position is obtained.

In the B-scan regime, the said translation stage is moved in steps after each T-scan to cover the depth range in a number of steps which determines the number of lines in the image frame, or the said translation stage is moved continuously in a time $T_B > T_H$ where the number of lines in the image frame is $T_B/T_H$, generating in this way a two dimensional map of reflectivity as a cross section through the object in a surface containing the optic axis and the T-scan contour.

In the C-scan regime, the transverse scanning means are used to move the beam angularly or laterally to cover a two dimensional pattern describing different shapes of T-scans in a time $T_C$ while the translation stage is kept fixed to generate a map of reflectivity for constant depth in the reference path of the interferometer.

In the 3D-scan regime, the translation stage is moved in small steps after each C-scan to cover a depth range or at a constant speed less than the ratio determined by dividing the depth resolution to $T_C$, covering the depth range in a time $T_{3D}$ and a number $T_{3D}/T_C$ of C-scans are stored and then used to generate a 3D image of the interior of the object.

In order to implement a compact apparatus configuration, no external phase modulator is employed for creating the carrier of the OCT signal. This has in fact allowed the reference path in FIG. 3 to be continuous for low losses and less vibration induced noise. Therefore, in the T-scan, B-scan or C-scan regimes of operation, the signal is encoded based on the phase modulation only, created by the movement of the transverse scanning means along the T-scan direction which determines the line in the raster of the B-scan or C-scan image, movement which determines modulation of the interference signal. The band pass filter in the block 26 is tuned on this modulation signal having a sufficient large band to insure sufficient transverse resolution in the T, B or C-scan image displayed by the displaying means. The low pass filter after the rectifier has also a similar band and both bands, of the band pass filter and of the low pass filter in the block 26 are adjusted experimentally as a trade-off between smearing the transverse pixel size in the image and the noise. Such an operation was disclosed in the U.S. Pat. No. 5,975,697 and the PCT patent WO00142735A1. Also, as explained in these patents, it is possible to increase the frequency of modulation of the interference signal generated by moving the object beam angularly or laterally along the T-scan contour. For instance, when using galvo or resonant scanners, by moving the incident beam on the scanning mirror away from the center of rotation, higher frequencies are generated when scanning the object. This is advantageous in order to better attenuate the low frequency noise components.

In the A-scanning regime, the transverse scanning means are fixed, deflecting the object beam to a fixed desired angular or lateral inclination, the translation stage is used to explore the depth range and the mapping apparatus acquires A-scans, i.e. one dimensional reflectivity profiles in depth. In opposition to the regimes above, the filter in the block 26 is tuned on the Doppler frequency $f_D=2v/\lambda$, where v is the translation stage velocity and $\lambda$ the central wavelength of the optical source used.

For example, a T-scan covering $N_T=250$ pixels requires a minimum bandwidth of $2N_T/T$, which for $T_H=1$ ms leads to 500 kHz. The interference signal is modulated in intensity by the object beam scanning the transverse pixels. The band pass filter has to accommodate like in any imaging problem a sufficient large band to display the pixels with little lateral smear. Therefore, a possible implementation of the band pass filter is as a combination of a low pass filter with a cut-off $2N_T/T_H=500$ kHz and a high pass filter with a cut-off of 50 kHz to eliminate the harmonics of vibration noise and the 1/f noise. In a typical B-scan imaging or C-scan imaging, $T_B$ is approximately $T_C=0.5$ s. To cover a 1 mm in depth in the B-scan regime, the stage 31 is moved at 2 mm/s.

The resultant image can be displayed in linear or logarithmic scale on grey or false colour coded format. The depth in the OCT channel is scanned by moving the stage 31 back and forward towards the object 15 or 16, changing the optical path in the object path.

All the elements within the dashed contour 40 belong to the core interferometer. All the elements within the block 30 are moved together by the stage 31. Optionally, the focusing adjustment element, 10, may be controlled from the computer, 28, via a translation stage 36, to maintain the focus in the object in synchronism with the position where the optical path difference is zero.

Optionally, when the object is the eye, a fixation lamp unit, 46, interleaved with the interface optics 14, is used for sending light towards the eye for guidance of the patient. Such a fixation lamp uses a beamsplitter or a dychroic filter by means known in the art to conveniently send light from a visible source to the eye, and move this source laterally by mechanical means, or by using a liquid crystal or a 2D LED array to move a spot, a cross or a star or a shaped luminous point laterally by electric means. The fixation lamp is powered by a power supply 47.

All optics connections are moved together which minimizes the vibration induced noise and polarization induced changes due to moving fiber leads. Electrical connections, similar to 25 are provided, 32, for the power supply 33 of the optical source, 34, for the signals driving the scanning head 11, and 35, for the signal driving the focusing adjustment 36 and 48 for the fixation lamp 46. Electrical loops 37, 38, 39, 41 and 49 are provided to allow for the free movement of the stage 31.

Placing all OCT elements on the moving stage, apart from the electronic processing blocks, presents the advantage that it eliminates all effects related to the movement of the fiber leads in previous art. The present disclosure reduces or eliminates polarisation effects, intensity variations, etc. with all optical signals processed on the moving stage 31. This has the advantage of profilometry of curved surfaces, where the coherence gate and the focus are in synchronism during the depth scanning.

The lens 10 and interface optics 14 can be implemented using reflective elements or combination of refractive and reflective elements. The signal driving the transverse scanner may have other forms different from triangle or sinusoid and the only essential feature for this operation is that the signal is periodic.

It will also be appreciated that instead of using the pulses 19' generated by the driver 19 it is possible to drive the display device 27 with a signal, 11', proportional with the position of the transverse scanners in the block 11 as described in a co-pending patent application entitled "Optical Mapping Apparatus with Adjustable Depth Resolution and Multiple Functionality", by A. Gh. Podoleanu, J. A. Rogers, G. Dobre, R. Cucu, D. A. Jackson, filed in the US Patent Office, Ser. No. 10/259,671, on Sep. 30, 2002.

The same principle could be applied for the depth direction, where the translation stage is driven by triangle signals or controlled by the PC 28 and the display means 27 is controlled by a position sensing element inside the translation stage, which delivers a position sensing signal, 31'.

The embodiment in FIG. 3 shows all optical splitters and delays in fiber. However, each splitter can also be implemented in bulk. So, the splitters 3 and 21, shown as directional couplers in FIG. 3 could be easily replaced by plate or cube beam-splitters. Similarly, the circulator 6 could also be replaced by a plate or a bulk beam-splitter, as shown in FIG. 9b. A circulator function could also be implemented in bulk as shown in FIG. 9a, using a polarization beam-splitter 68 followed in the path 7 by a quarter wave plate 67 according to principles known by those skilled in the art. If light from the first output of the first optical splitter is linearly polarized by the polarizer 66, then light is transmitted to one output of the splitter 68 only. Light is circularly polarized by the quarter wave plate 67 oriented at 45° with respect to the direction of the linear polarisation of the light immediately after 68. From a minor, light is returned as a circularly polarized light of opposite handedness and after 67 is linearly polarized along a rectangular direction to that of the incident light to 68 and therefore light will now appear at the other input of the splitter 68, i.e. all light will be transferred to path 20.

Also, the delay 4' can be implemented by using folded free space paths known for those skilled in the art and all the fiber connections, 2, 4, 5 and 20 could be free space paths.

A problem with using OCT imaging systems is that due to the low value of the coherence length, finding the position where the OPD=0 may be difficult. The placement of the object where OPD=0 is found by moving the object along the optic axis to and from the translation stage 30 and watching for the image on the screen of the PC 28. If the object is moved too fast, the position of OPD=0 may be missed. As an additional disadvantage, if the object is the eye, this procedure cannot be employed by the user on her or his own. Two persons are required. The invention provides for a solution in this respect, where an AF amplifier block 55 sends the rectified OCT signal towards a loudspeaker. In this way, self-imaging is possible, procedure useful in the adjustment of the apparatus, where adjustment of the eye position can be executed by following the sound emitted by the loudspeaker of 55, with no need of a second person.

Figure 4:
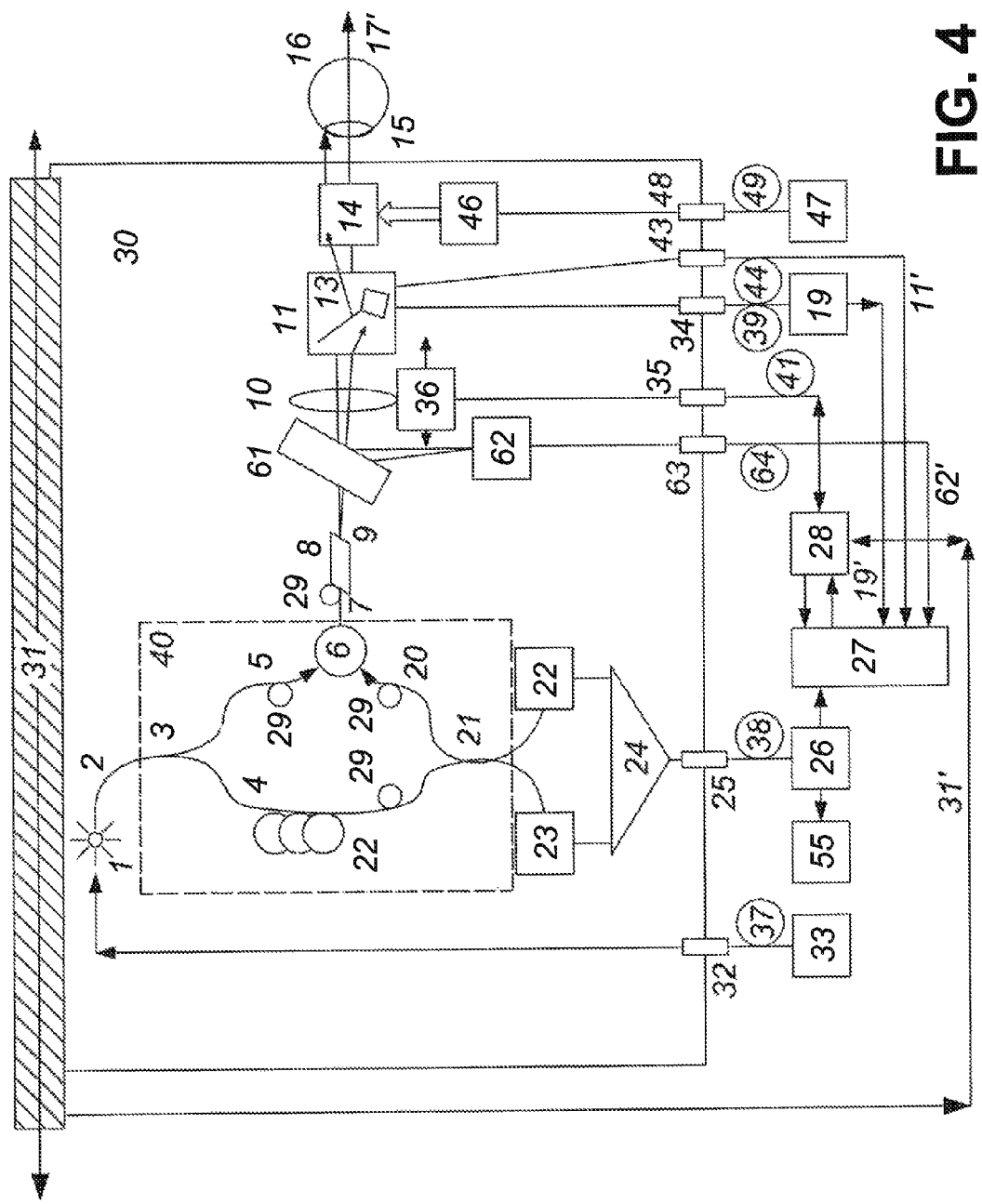
FIG. 4 shows, shows, in diagrammatic form, a second embodiment of the compact high resolution mapping apparatus providing an OCT and a confocal image simultaneously.

Another embodiment of the present invention is shown in FIG. 4. In addition to the elements in the embodiment presented in FIG. 3, a confocal optical splitter, 61 is placed in the object path 9 leading to the focusing element 10. This diverts some of the light returned from the object 15 or 16 to a confocal receiver, 62. A confocal receiver is implemented using a pinhole and a high gain photodetector amplifier, equipped with an avalanche photodiode or a photomultiplier, by means known in the art and described in the copending application "Optical mapping apparatus with adjustable depth resolution and multiple functionality", by A. Gh. Podoleanu, J. A. Rogers, G. Dobre, R. Cucu, D. A. Jackson, U.S. application Ser. No. 10/259,671, Sep. 30, 2002 (International PCT application: PCT/CA03/00993.). In the embodiment in FIG. 4 the splitter 61 and confocal receiver 62 are mounted on the same stage 30 as the other optical elements and moved together. A flexible coaxial cable, via connector 63 and loop 64 delivers the signal from the output of the confocal receiver channel to the displaying means 27, which could be implemented for example by a two input digital frame grabber under the control of the PC control 28. Preferably, the splitter 61 is a plate beam-splitter, sufficiently thick to avoid multiple reflections being returned to the fiber end 8, as explained in the co-pending application "Optical Mapping Apparatus with Optimised OCT Configuration", by Adrian Podoleanu, George Dobre, Radu Cucu, John Rogers, David Jackson, USA Application, May 2003, number unknown. This splitter has an optimum splitting ratio as explained in the U.S. Pat. No. 5,975,697 to insure similar signal to noise ratios in the two channels, OCT and confocal. The splitting ratio could be found experimentally as 1 to 18% power diverted to the confocal receiver 62 from the power returned from the object 15 or 16.

The confocal splitter 61 is used in transmission by the OCT signal and in reflection by the confocal channel in FIG. 2, however it should be obvious for those skilled in the art and equally, the optical splitter 61 can be used in transmission by the confocal signal and in reflection by the OCT signal without departing from the scope of the invention.

The confocal optical splitter 61 can also be mounted between the second optical splitter 6 and the third optical splitter 21 as shown in FIG. 3. The alike elements carry the same numbers as in the embodiments in FIGS. 1 and 2. If the confocal optical splitter 61 is implemented in fiber, as shown in FIG. 3 by a single mode directional coupler, then the other input 45 is terminated with fiber cleaved at an angle or with an angled cleaved connector such as those known in the art, FC/APC or equivalent, in order to avoid multiple reflections among different fiber ends of the optical splitters used in the core interferometer 40. The advantage of placing the confocal splitter 61 between the second and the third optical splitter is in less loss of object power sent to the object 15 or 16.

Two optical sources, 1 and 1' launch light into the input 2 of the first optical splitter 3 via a fifth optical splitter 71. The sources 1 and 1' should have substantially different wavelengths in those cases where the wavelength of the source 1 to be used for the OCT is such long, as the sensitivity of Silicon avalanche photodiodes or photomultipliers to be used in the confocal receiver 62 is too low. For instance, when the wavelength of the source 1 is longer than 1000 nm, then a source 1' which could be a low coherence source or a highly coherent source such as a laser, emitting on a wavelength shorter than 900 nm could be employed, wavelength which could be advantageously processed by low cost Silicon avalanche photodiodes or photomultiplier tubes. When the wavelengths of the sources 1 and 1' are sufficiently different, then the confocal optical splitter 61 and the fifth optical splitter 71 could use WDM couplers or dychroic filters if implemented in bulk, means known in the art. This will minimize the losses at the OCT wavelength of the source 1 and at the confocal receiver wavelength of the source 1'.

Figure 5:
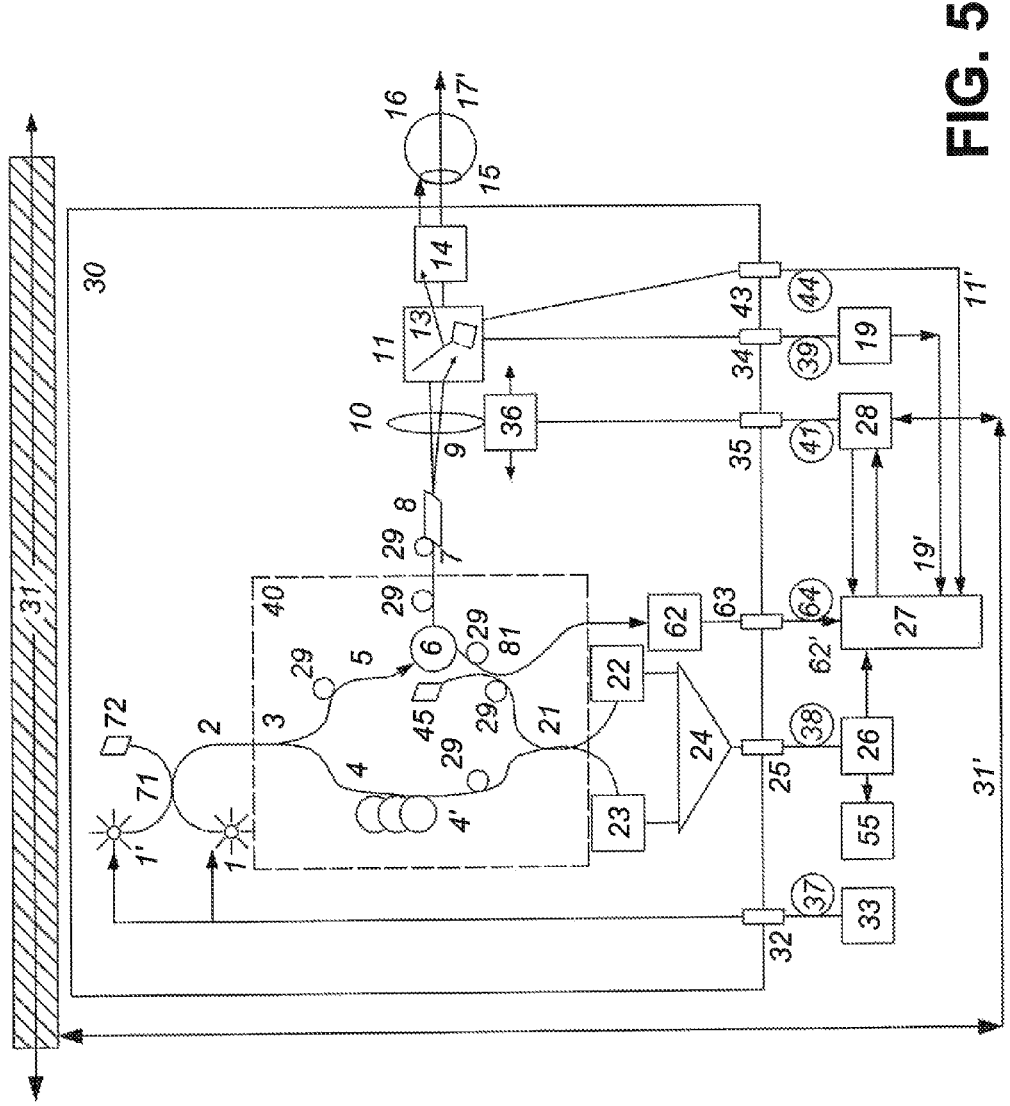
FIG. 5 shows, in diagrammatic form, a third embodiment of the compact high resolution mapping apparatus providing an OCT image, which insures less deviation of the focusing gate depth from the coherence gate depth.

It is obvious that the utilization of two sources 1 and 1' and of WDM or dychroic filters as described here in connection to the embodiment in FIG. 5 is equally applicable for the embodiment in FIG. 4 where the confocal optical splitter was placed between the second optical splitter 6 and the transverse scanning block 11.

The technique of using different wavelengths for the two channels, OCT and confocal was disclosed in the copending application "Optical mapping apparatus with adjustable depth resolution and multiple functionality", by A. Gh. Podoleanu, J. A. Rogers, G. Dobre R. Cucu, D. A. Jackson, U.S. application Ser. No. 10/259,671, Sep. 30, 2002 (International PCT application: PCT/CA03/00993.)

Figure 6:
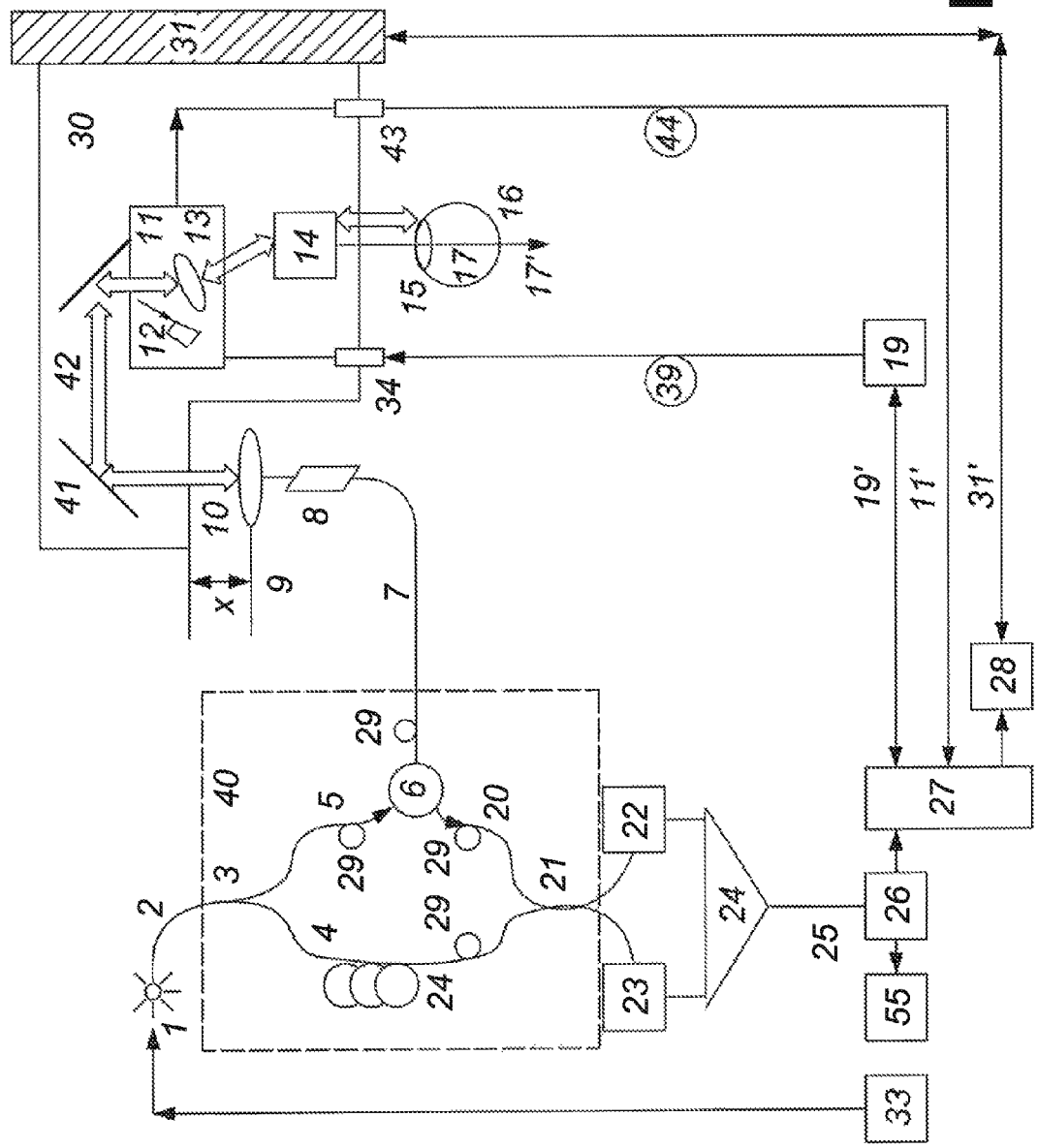
FIG. 6 shows, in diagrammatic form, a fourth embodiment of the compact high resolution mapping apparatus providing simultaneously an OCT image and a confocal image, which insures less deviation of the focusing gate depth from the coherence gate depth.

Another embodiment of the present invention is shown in FIG. 6. The alike elements carry the same numbers as in the previous embodiments. The circulator output along the path 7, shown in fiber in FIG. 6, is terminated with a fiber end connector cleaved at an angle, 8. which launches light towards the mirrors 41 and 42 which redirect the light in the opposite direction towards the scanning head 11. In this embodiment, the support 30 moved by the translation stage 31 contains the mirrors 41, 42, the scanning head 11 and the interface optics 14. For a movement of the stage 31 by x, towards the object 15 or 16, the focus point moves inside the object by nx and the optic path changes by $n^2x$. Due to the round trip path, the object path increases by $2n^2x$. The optic path difference changes by $2n^2x-4x$. This represents an insignificant value if n is approximately 1.41. With this assumption, the movement of the coherence gate is approximately synchronous with the movement of the focus gate in tissue. In comparison to the implementation described in the Schmitt's paper mentioned above, the embodiment in FIG. 6 is simpler as it alters object path only and the reference path can be routed separately and away from the moving elements. This novel dynamic focus procedure is consistent with the aim of this disclosure for a compact system, easy to assemble, as here, only the object path is folded. The implementation in FIG. 6 allows a continuous fiber connection in the reference path with advantages in the assembly time of the apparatus. Evidently, no fiber optic lead is involved in the moving parts which is advantageous in terms of noise or polarization induced noise. As commented in relation to the embodiment in FIG. 3, the core interferometer enclosed within the dashed area 40 can be equally implemented in free space or hybrid, as a combination of single mode couplers or bulk beam-splitters with the second optical splitter 6 implemented in bulk or in fiber, either as a simple splitter as shown in FIG. 9*b* or as a bulk circulator as shown in FIG. 9*a*.

This embodiment has the advantage that for the same movement x of the stage 31, the OPD changes by 4x instead of 2x in FIG. 3-5.

Figure 7:
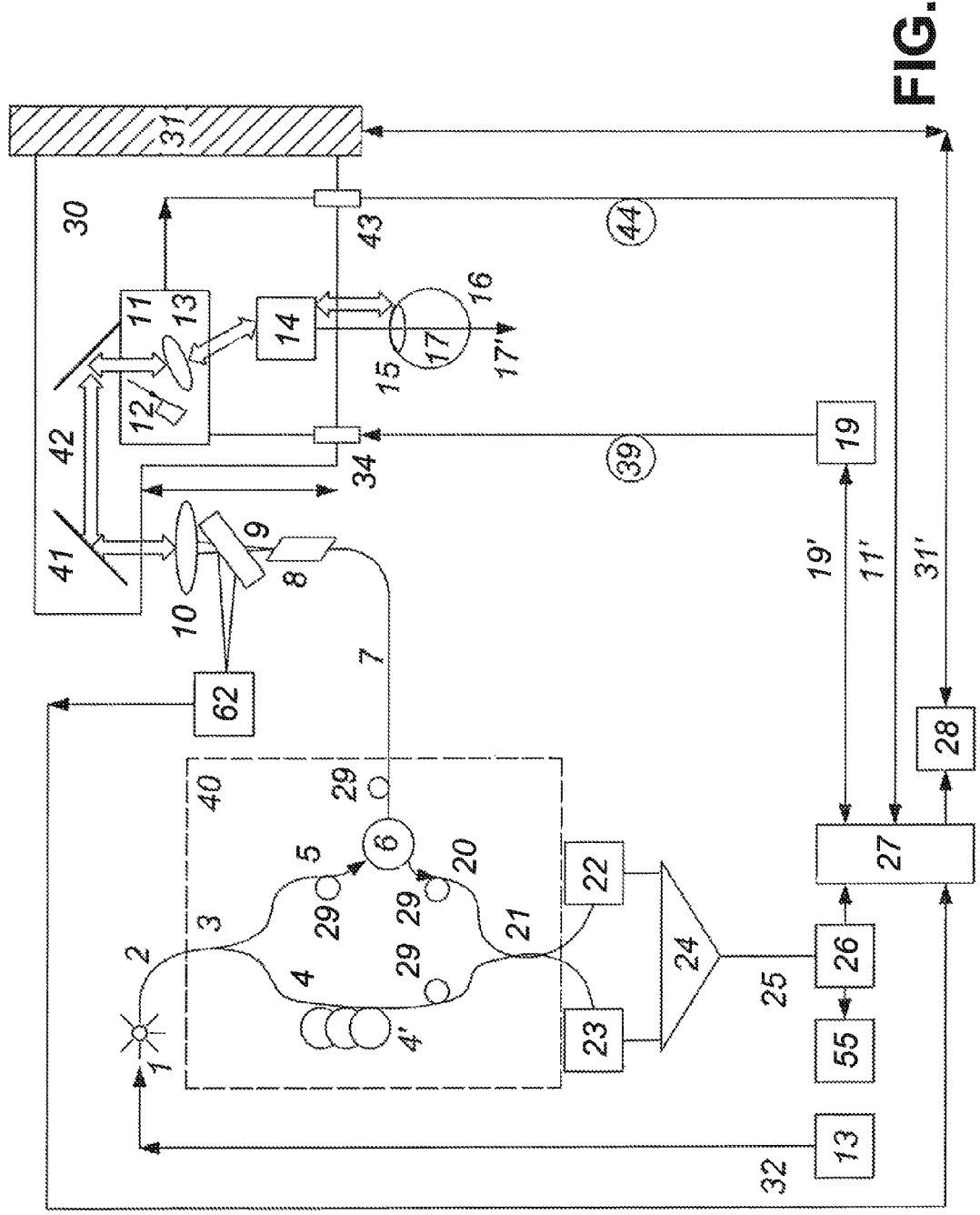
FIG. 7 shows, in diagrammatic form, a fifth embodiment of the compact high resolution mapping apparatus providing simultaneously an OCT image and a confocal image, which insures less deviation of the focusing gate depth from the coherence gate depth.

A version of the embodiment in FIG. 6 is shown in FIG. 7. In addition to the elements in the embodiment presented in FIG. 6, a confocal optical splitter, 61 is placed in the object path 9 leading to the 2D transverse scanner 11. This diverts some of the light returned from the object 15 or 16 to a confocal receiver, 62. A confocal receiver is implemented using a pinhole and a high gain photodetector amplifier, equipped with an avalanche photodiode or a photomultiplier, by means known in the art and described in the copending application "Optical mapping apparatus with adjustable depth resolution and multiple functionality", by A. Gh. Podoleanu, J. A. Rogers, G. Dobre, R. Cucu, D. A. Jackson, U.S. application Ser. No. 10/259,671, Sep. 30, 2002 (International PCT application: PCT/CA03/00993.)). The splitter 61 and confocal receiver 62 could be mounted on the same stage 30 moved by the translation stage 31, anywhere between the mirrors 41 and 42, or before mirror 41, or after mirror 42, or fixed between the focusing element 10 and the moving mirror 42. If placed on the stage, then a flexible coaxial cable, via connector 63 and loop 64 should be used to delivers the signal from the output of the confocal receiver 62 to the displaying means 27, as explained in connection with the embodiment in FIG. 2. Preferably, the confocal optical splitter and confocal receiver are fixed, placed outside the stage 30, as shown in FIG. 7, in which case a coaxial cable 62' connects the confocal receiver 62 to the dual input displaying means 27, which could be implemented for example by a two input digital frame grabber under the control of the PC 28.

Preferably, the splitter 61 is a plate beam-splitter, sufficiently thick to avoid multiple reflections being returned to the fiber end 8, as explained in the co-pending application "Optical Mapping Apparatus with Optimised OCT Configuration", by Adrian Podoleanu, George Dobre, Radu Cucu, John Rogers, David Jackson, USA Application, May 2003, number unknown. This splitter has an optimum splitting ratio as explained in the U.S. Pat. No. 5,975,697 to insure similar signal to noise ratios in the two channels, OCT and confocal. The splitting ratio could be found experimentally as 1 to 18% power diverted to the confocal receiver 62 from the power returned from the object 15 or 16.

Figure 8:
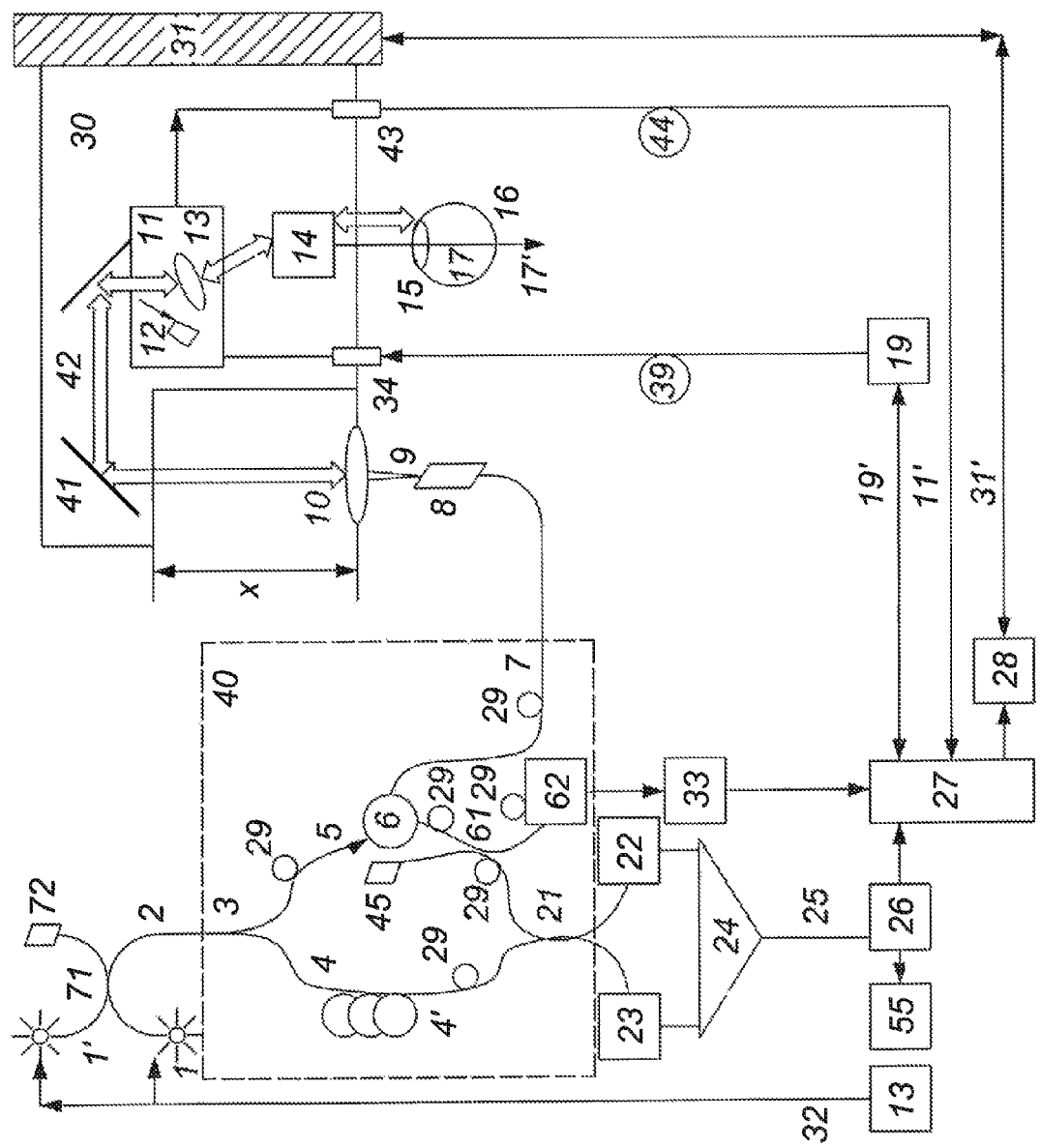
FIG. 8 shows, in diagrammatic form, a version of the embodiment in FIG. 5 with a different position of the optical splitter of the confocal receiver.

The confocal optical splitter 61 can also be mounted between the second optical splitter 6 and the third optical splitter 21 as shown in FIG. 8. The alike elements carry the same numbers as in the embodiment in FIGS. 6 and 7. If the confocal optical splitter 61 is implemented in fiber, as shown in FIG. 8 by a single mode directional coupler, then the other input 45 is terminated with fiber cleaved at an angle or with an angled cleaved connector such as those known in the art, FC/APC or equivalent, in order to avoid multiple reflections among different fiber ends of the optical splitters used in the core interferometer 40. The advantage of placing the confocal splitter 61 between the second and the third optical splitter is in less loss of object power sent to the object 15 or 16.

Optionally, as described in connection to the embodiment in FIG. 5, two sources 1 and 1' of different wavelengths can be used to launch light into the input 2 of the first optical splitter 3 via a fifth optical splitter 71. The sources 1 and 1' should have substantially different wavelengths in those cases where the wavelength of the source 1 to be used for the OCT is such long, as the sensitivity of Silicon avalanche photodiodes or photomultipliers to be used in the confocal receiver 62 is to low. For instance, when the wavelength of the source 1 is longer than 1000 nm, then a source 1' which could be a low coherence source or a highly coherent source such as a laser, emitting on a wavelength shorter than 900 nm could be employed, wavelength which could be advantageously processed by low cost Silicon avalanche photodiodes or photomultiplier tubes. When the wavelengths of the sources 1 and 1' are sufficiently different, then the confocal optical splitter 61 and the fifth optical splitter 71 could use WDM couplers or dychroic filters if implemented in bulk, means known in the art. This will minimize the losses at the OCT wavelength of the source 1 and at the confocal receiver wavelength of the source 1'.

The technique of using different wavelengths for the two channels, OCT and confocal was disclosed in the copending application "Optical mapping apparatus with adjustable depth resolution and multiple functionality", by A. Gh. Podoleanu, J. A. Rogers, G. Dobre R. Cucu, D. A. Jackson, U.S. application Ser. No. 10/259,671, Sep. 30, 2002 (International PCT application: PCT/CA03/00993.)

When the second optical splitter 6 is implemented as a two by two splitter, as shown in FIG. 9*b*, an alternative interferometer core 30 can be devised as shown in FIGS. 10 and 11.

FIG. 9*b* shows the utilization of a two by two splitter in the embodiments disclosed in FIGS. 3 to 8, where only three ports are used, connected to the paths 5, 7 (towards to object) and towards path 20. The fourth is terminated on an FC/APC connector, 8', or with fiber cleaved at an angle to avoid stray reflections and keep noise low. In FIGS. 10 and 11, all four ports of a two by two splitter are used. FIG. 10 discloses such an embodiment where light from the optical source 1 is injected direct into the second splitter 6. In opposition to the use of a two by two splitter as the second splitter 6 in the embodiments in FIGS. 3 to 8, here all four ports are used.

Similar to the previous embodiments, light retroreflected from the object is sent via path 20 towards the third optical splitter 21. Here the fourth port, unused in previous embodiments is employed to send light from the optical source 1 towards the reference path 4. The splitter 6 has a splitting ratio to optimize the signal to noise ratio. Such an analysis has been presented in our co-pending application "Optical Mapping Apparatus with Optimised OCT Configuration", by Adrian Podoleanu, George Dobre, Radu Cucu, John Rogers, David Jackson, USA Application, May 2003, number unknown.

The embodiment in FIG. 10 of the core interferometer 40 could equally be used in any of the embodiments disclosed in FIGS. 3, 4, 6 and 7.

The embodiment in FIG. 11 of the core interferometer 40 is a version of the embodiment in FIG. 10 where the confocal optical splitter 61 is incorporated between the $2^{nd}$ splitter 6 and the third splitter 21, to divert light towards the confocal receiver. This embodiment could equally be used in any of the embodiments disclosed in FIGS. 5 and 8.

It should be obvious for those skilled in the art that while the examples above referred to objects with one convex or concave part, equally, everything said here is valid for complex shaped objects, where the front surface exhibits several spurs, domes, peaks and craters. In this case, the method of focus optimisation discussed should be applicable to each such curved volume.

For such complex objects, the imaging should proceed in two steps, $1^{st}$ the profilometry of the first surface is constructed using that adjustment where the focus surface and coherence gate surface coincide in air. The profile is then used in the $2^{nd}$ step, where in order to enhance the strength of the signal acquired from inside the object and reduce the reflectivity of the first interface, the focus is adjusted in such a way as to place the focus surface F closer to the stage than the coherence gate surface C for spurs and place the coherence gate surface C closer to the stage 30 than the focus surface F for craters.

Thus, it is apparent that there has been provided, in accordance with the present invention, an optical mapping apparatus and method which fully satisfies the means, objects, and advantages set forth hereinbefore. Therefore, having described specific embodiments of the present invention, it will be understood that alternatives, modifications and variations thereof may be suggested to those skilled in the art, and that it is intended that the present specification embrace all such alternatives, modifications and variations as fall within the scope of the appended claims.

We claim:

1. An optical coherence tomography (OCT) apparatus comprising:
   an interferometer having a reference arm and an object arm, said object arm providing an object beam for scanning of an object;
   wherein a coherence gate is determined by the optical path difference between the reference arm and the object arm for returning an OCT signal from the object;
   said interferometer including optical components mounted on a common translation stage for scanning an object with said object beam;
   said optical components being configured to bring said object beam to a focus;
   said translation stage being displaceable towards and away from said object to permit scanning said object in an axial direction;
   said optical components being configured on said translation stage to permit displacement of the translation stage in said axial direction with said optical components remaining in a fixed relationship;
   wherein said optical components are configured to maintain said coherence gate in approximate coincidence with said focus during axial displacement of said translation stage with a variable error $\epsilon$ between said coherence gate and said focus; and
   wherein an initial error $\epsilon_0$ in a reference plane is set at a value computed to reduce the variable error $\epsilon$ during axial and transverse scanning of the object over an axial range of interest taking into account the refractive index of the object and its curvature.

2. An optical coherence tomography (OCT) apparatus as claimed in claim 1, wherein said reference plane is located at a position selected from the group consisting of: outside said object and a front plane of said object.

3. An optical coherence tomography (OCT) apparatus as claimed in claim 1, wherein said initial error $\epsilon_0$ is determined in accordance with the equation $$z_0 = \epsilon_0/(n^2 - 1)$$

wherein $z_0$ is a target depth within the object at which actual coincidence occurs and n is the refractive index of the object.

4. An optical coherence tomography apparatus as claimed in claim 1, wherein said interferometer comprises an additional output port for sending light returned from the object to a confocal receiver.

5. An optical coherence tomography (OCT) apparatus comprising an optical source, an interferometer having an object arm generating an object beam and a reference arm generating a reference beam, and in the object arm, an optical fiber connection between the interferometer and a focus element, a transverse scanner and interface optics for scanning an object with said object beam, and a processor for generating an OCT image from an OCT signal returned by said interferometer, and wherein at least said fiber connection, focus element, scanner and interface optics are mounted on a common translation stage displaceable towards and away from said object to perform axial scanning in the OCT apparatus, said OCT apparatus having a coherence gate;
   and where the focus element is configured depending on a curvature of the object, to substantially diminish the error path within the object between the depth position of the optimum focus and that of a point sampled by the OCT coherence gate during transverse and axial scanning.

6. An optical coherence tomography apparatus as claimed in claim 5, further comprising a confocal imaging system for generating a second image of said object, and wherein said confocal imaging system comprises a confocal splitter and confocal receiver, each of which is mounted on said common translation stage.

7. The optical coherence tomography apparatus of claim 6, wherein said second image is simultaneously produced and displayed with the said OCT image and is pixel to pixel correspondent.

8. An optical coherence tomography apparatus as claimed in claim 5, where said focusing element is equipped with a control element for displacing said focusing element in such a way as to maintain the focus in coincidence with a position in the object where the optical path difference between said reference beam and said object beam is substantially zero.

9. An optical coherence tomography apparatus as claimed in claim 5, wherein the components of said apparatus that are mounted on said common translation stage are connected to the remainder of said apparatus only by flexible electric cables.

10. An optical coherence tomography apparatus as claimed in claim 5, wherein the transverse scanner and said common translation stage supports interface optics, reflectors for a 180° folded object path, and wherein said reflectors receive an optical output beam from a second optical splitter via a launcher which is placed the same side of the translation stage as the object in such a way that when the stage moves, the variation of the optical path from the launcher to the stage substantially equals the variation of the path measured from the interface optics on the stage up to a scattering point where signal is collected from the volume of the object.

11. An optical coherence tomography apparatus as claimed in claim 5, wherein:
   said interferometer has a core interferometer which has an input port for radiation source, an output object beam port for the object beam and two output interference ports and includes means for dividing the input beam along an object arm and a reference beam along a reference arm each starting at the respective first output and second output of a first optical splitter;
   light from the first output of the first optical splitter is sent to a first input port of a second optical splitter and the light at one of the corresponding output ports of the second optical splitter is sent towards the said output object beam port of the interferometer and the port of the second optical splitter, wherein light traveling from the output object beam port of the interferometer originates is optically connected to the first input of a third optical splitter and where the second input of the third optical splitter receives light from the second output of the first optical splitter via a delay line and where the outputs of the third optical splitter provide signals to the two said output interference ports of the interferometer;
   a reference path is defined as the path taken by the reference beam from the first optical splitter via the delay line up to the third splitter;
   the delay line is adjusted to match the optical length of the reference path to the length of an object path; and
   a polarization controller is provided to match an orientation of the polarization in the object and reference paths.

12. An optical coherence tomography apparatus as claimed in claim 11, further comprising focusing means synchronously adjusted with the movement of the translation stage to maintain in focus the point where the optical path length of the reference path is matched to the path length of the object path.

13. An optical coherence tomography apparatus as claimed in claim 5, wherein:
   said interferometer has a core interferometer which has an input port for a radiation source, and first and second output object beam ports for the object beam and two output interference ports and includes means for dividing an input beam along an object arm and a reference beam along a reference arm each starting at the respective first output and second output of a first optical splitter;
   light from the first output of the first optical splitter is sent to a first input port of a second optical splitter and the light at a corresponding output port of the second optical splitter is sent towards the first output object beam port of the interferometer and the port of the second optical splitter where light traveling from the first output object beam port of the core interferometer originates from is optically connected to the first input of a confocal optical splitter and the first output of the confocal optical splitter is optically connected to the first input of a third optical splitter and where the second output of the confocal optical splitter sends light towards the second output object beam port of the core interferometer and the second input of the third optical splitter receives light from the second output of the first optical splitter via a delay line and where the outputs of the third optical splitter provide signals to the two said output interference ports of the core interferometer;
   a reference path is defined as the path taken by the reference beam from the first optical splitter via the delay line up to the third splitter;
   an object path is defined as the path taken by the object beam from the first splitter, via the second splitter, a focusing element, scanner means, and interface optics to a depth inside the object to be investigated and therefrom back via the interface optics, scanner, focusing element towards the second splitter, confocal optical splitter up to the third splitter;
   the delay line is adjusted to match the optical length of the reference path to the length of the object path; and
   a polarization controller is provided to match an orientation of the polarization in the object and reference paths.

14. An optical coherence tomography apparatus as claimed in claim 13, wherein focusing means are synchronously adjusted with the movement of the translation stage to maintain in focus the point where the optical path length of the reference path is matched to the path length of the object path.

15. An optical coherence tomography apparatus as claimed in claim 5, wherein:
   said interferometer comprises means for dividing an input beam along an object arm and a reference beam along a reference arm starting at the respective first output and second output of a second optical splitter;
   light from the first output of the second optical splitter is sent to the first output object beam port for the object beam of the core interferometer and the second output of the second optical splitter is optically connected via a delay line to the first input of a third optical splitter whose outputs sends light towards the two output interference ports of a core interferometer and where the second input of the second optical splitter is optically connected to the first input of a confocal optical splitter and the first output of a confocal optical receiver is optically connected to the second input of the third optical splitter and the second output of the confocal optical splitter is connected to the second object beam port for the object beam of the core interferometer;
   a reference path is defined as the path taken by the reference beam from the second optical splitter via the delay line up to the third optical splitter;
   an object path is defined as the path taken by the object beam from the second splitter, via the focusing element, transverse scanning means, interface optics up to a depth inside the object to be investigated and therefrom back via the interface optics, transverse scanning means, focusing element towards the second optical splitter, confocal optical splitter and then up to the third optical splitter;
   the delay line is adjusted to match the optical length of the reference path to the length of the object path; and
   a polarization controller is provided to match an orientation of the polarization in the object and reference paths.

16. An optical coherence tomography apparatus as claimed in claim 15, wherein focusing means are synchronously adjusted with the movement of the translation stage to maintain in focus the point where the optical path length of the reference path is matched to the path length of the object path.

17. An optical coherence tomography apparatus as claimed in claim 5, wherein said scanner comprises a transverse scanning means split into a line scanner and a frame scanner which are interleaved with elements of interface optics for independent control of curvature of a scanned surface along rectangular directions to an optic axis.

18. In an optical coherence tomography (OCT) apparatus comprising an optical source, an interferometer having an object arm generating an object beam and a reference arm generating a reference beam, and in the object arm, a focus element, a transverse scanner for scanning an object with said object beam, and a processor for generating an OCT image from an OCT signal returned by said interferometer, wherein the improvement wherein comprises at least said optical source, said interferometer, and said transverse scanner are mounted on a common translation stage displaceable towards and away from said object to perform axial scanning in the OCT apparatus, said OCT apparatus having a coherence gate, and where the focus element is configured depending on a curvature of the object, to substantially diminish the error path within the object, between the depth position of the optimum focus and that of a point sampled by the OCT coherence gate during transverse and axial scanning.

19. An optical coherence tomography apparatus as claimed in claim 18, wherein light from an output object beam port of said interferometer is sent to a first input of said confocal splitter and then via a focusing element towards the transverse scanner; and light returned from the object is directed to a second input of the confocal splitter whereby one portion of said returned light is sent to a confocal receiver and another portion of said returned light is returned to said interferometer.

20. An optical coherence tomography apparatus as claimed in claim 18, wherein said optical radiation source is synthesized from two sources, a first source of low coherence, with a coherence length less than 1 mm, and a second source, of low or high coherence, where the second optical source has a substantially different central wavelength than the wavelength of the first optical source, chosen in a range where the photodetector in a confocal receiver has maximum sensitivity and where the two sources are coupled to the input of a core interferometer via an optical splitter, and where this optical splitter and a confocal splitter are implemented using a free space bulk splitter or a fiber directional coupler or a WDM coupler.

* * * * *